United States Patent [19] [11] Patent Number: 4,482,546
Takahashi et al. [45] Date of Patent: Nov. 13, 1984

[54] FUNGICIDAL N-PHENYLCARBAMATES

[75] Inventors: Junya Takahashi, Nishinomiya; Toshiro Kato, Takarazuka; Katsuzo Kamoshita, Osaka, all of Japan

[73] Assignee: Sumitomo Chemical Company, Limited, Osaka, Japan

[21] Appl. No.: 367,404

[22] Filed: Apr. 12, 1982

[30] Foreign Application Priority Data

Apr. 16, 1981 [JP] Japan ................................. 56-58303
Nov. 6, 1981 [JP] Japan ................................. 56-178509

[51] Int. Cl.$^3$ ...................... A01N 57/30; A01N 47/10; C07C 125/063
[52] U.S. Cl. ............................. 424/211; 260/455 A; 260/465 D; 424/272; 424/273 B; 424/274; 424/300; 560/27; 560/29
[58] Field of Search ................... 260/455 A, 465 D; 560/29, 27; 424/300, 272, 211, 273 B, 274

[56] References Cited

U.S. PATENT DOCUMENTS 3,660,465  5/1972  Baker .............................. 424/300 X
3,800,037  3/1974  Martin et al. .................... 424/186
3,852,332 12/1974  Cross et al. ...................... 560/29

FOREIGN PATENT DOCUMENTS 2921130 12/1980 Fed. Rep. of Germany .

OTHER PUBLICATIONS

Chemical Abstracts, vol. 28, p. 4045 (Arch. Pharm., 272, 221-235 (1934)).
Chemical Abstracts, vol. 78, 58392f (1973) (French Patent M 8200).
Derwent's "RINGDOC" abstract of JA-29277/69.
Derwent's "RINGDOC" abstract of JA-001103.
Derwent's "RINGDOC" abstract of DT-2330-242.
Weed Research, vol. 20, pp. 249-254 (1980).
C. R. Acad. Sc. Paris, t. 289, 691-693 (S'erie D).

Primary Examiner—Dolph H. Torrence
Attorney, Agent, or Firm—Birch, Stewart, Kolasch & Birch

[57] ABSTRACT

Use of an N-phenylcarbamate of the formula:

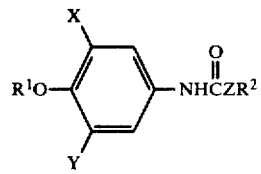

as a fungicidal agent against phytophatogenic fungi, particularly strains which are resistant to benzimidazole thiophanate fungicides and/or cyclic imide fungicides.

67 Claims, No Drawings

FUNGICIDAL N-PHENYLCARBAMATES

This invention relates to fungicidal N-phenylcarbamates.

Benzimidazole thiophanate fungicides such as Benomyl (methyl-1-(butylcarbamoyl)benzimidazol-2-ylcarbamate), Fubelidazol (2-(2-furyl)benzimidazole), Thiabendazole (2-(4-thiazolyl)benzimidazole), Carbendazim (methyl benzimidazol-2-ylcarbamate), Thiophanate-methyl (1,2-bis(3-methoxycarbonyl-2-thioureido)benzene), Thiophanate (1,2-bis(3-ethoxycarbonyl-2-thioureido)benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene are known to show an excellent fungicidal activity against various plant pathogenic fungi, and they have been widely used as agricultural fungicides since 1970. However, their continuous application over a long period of time results in phytopathogenic fungi becoming tolerant to the fungicides, whereby their plant disease-preventive effect is much lowered. Further, the fungi which gain tolerance to certain kinds of benzimidazole thiophanate fungicides also show considerable tolerance to some other kinds of benzimidazole thiophanate fungicides. Thus, they are apt to obtain cross-tolerance. Therefore, if any material decrease of their plant disease-preventive effect in certain fields is observed, their application to such fields has to be discontinued. But, it is often observed that the density of drug-resistant organisms is not decreased even long after the discontinuation of the application. Although other kinds of fungicides have to be employed in such case, only few are as effective as benzimidazole thiophanate fungicides in controlling various phytopathogenic fungi. Cyclic imide fungicides such as Procymidone (3-(3',5'-dichlorophenyl)-1,2-dimethylcyclopropane-1,2-dicarboximide), Iprodione (3-(3',5'-dichlorophenyl)-1-isopropylcarbamoylimidazolidine-2,4-dione), Vinchlozoline (3-(3',5'-(dichlorophenyl)-5-methyl-5-vinyloxazolidin-2,4-dione), ethyl (RS)-3-(3',5'-dichlorophenyl)-5-methyl-2,4-dioxooxazolidine-5-carboxylate, etc., which are effective against various plant diseases, particularly those caused by *Botrytis cinerea*, have the same defects as previously explained with respect to the benzimidazole thiophanate fungicides.

In C.R. Acad. Sc. Paris, t. 289, S'erie D, pages 691–693 (1979), it is described that such herbicides as Barban (4-chloro-2-butynyl N-(3-chlorophenyl)carbamate), Chlorobufam (1-methyl-2-propynyl N-(3-chlorophenyl)carbamate), Chloropropham (isopropyl N-(3-chlorophenyl)carbamate) and Propham (isopropyl N-phenylcarbamate) exhibit a fungicidal activity against certain organisms tolerable to some of the benzimidazole thiophanate fungicides. As readily understood from their herbicidal use, however, their foliar application to crop plants as fungicides causes serious chemical injury thereon. In addition, their fungicidal activity against the drug-resistant fungi is not strong enough, and hence they can not be used as a fungicide.

As a result of the study seeking a new type of fungicides, it has now been found that N-phenylcarbamates of the formula:

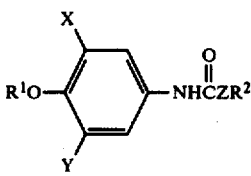

wherein X and Y which may be the same of different, are each a halogen atom, a lower alkyl group, a lower alkenyl group, a lower cyanoalkenyl group, a lower alkynyl group, a lower alkoxy group, a cyano group, a lower alkyl group substituted with at least one member selected from the group consisting of halogen, hydroxyl and cyano, or a group of the formula:

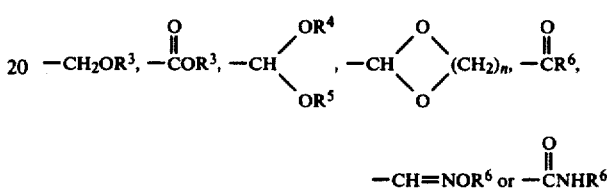

in which $R^3$ is a lower alkyl group, a lower alkenyl group, a lower alkynyl group or a lower haloalkyl group, $R^4$ and $R^5$ are, same or different, each a lower alkyl group, $R^6$ is a hydrogen atom or a lower alkyl group, n is 2, 3 or 4, Z is an oxygen atom or a sulfur atom, $R^1$ is a lower alkyl group, a lower alkenyl group, a lower alkynyl group or a lower alkyl group substituted with at least one member selected from the group consisting of halogen, lower alkoxy and lower cycloalkyl and $R_2$ is a $C_1$–$C_8$ alkyl group, a $C_3$–$C_8$ alkenyl group, a $C_3$–$C_8$ alkynyl group, a lower cycloalkyl group, a lower haloalkenyl group, a lower haloalkynyl group or a lower alkyl group substituted with at least one member selected from the group consisting of halogen, cyano, lower alkoxy, lower alkenyloxy, lower haloalkoxy, phenoxy, lower aralkyloxy and lower cycloalkyl, show an excellent fungicidal activity against plant pathogenic fungi which have developed resistance to benzimidazole thiophanate fungicides and/or cyclic imide fungicides. It is notable that their fungicidal potency against the organisms tolerant to benzimidazole thiophanate fungicides and/or cyclic imide fungicides (hereinafter referred to as "drug-resistant fungi" or "drug-resistant strains") is much higher than that against the organisms sensitive to benzimidazole thiophanate fungicides and/or cyclic imide fungicides (hereinafter referred to as "drug-sensitive fungi" or "drug-sensitive strains").

All the N-phenylcarbamates (I) are novel compounds except ethyl N-(3,4,5-trimethoxy)phenylcarbamate, ethyl N-(3,4,5-triethoxy)phenylcarbamate and propargyl N-(4-methoxy-3,5-dibromo)phenylcarbamate. These compounds have been known, but it has not been known or reported that they have fungicidal activity or that they are useful as fungicides [DT-OS 2,041,986, French patent M8200, Arch. Pharm., 272, 221–235 (1934)].

Thus, the present invention provides a fungicidal composition which comprises, as an active ingredient, a fungicidally effective amount of the N-phenylcarbamate (I) and an inert carrier or diluent. It also provides a combination composition comprising as active ingredients the N-phenylcarbamate (I) together with a benzimidazole thiophanate fungicide and/or a cyclic imide fungicide, which is fungicidally effective against not only drug-sensitive fungi but also drug-resistant fungi, and hence particularly effective for the prevention of plant diseases. It also provides a method of controlling plant pathogenic fungi including drug-resistant strains and drug-sensitive strains applying a fungicidally effective amount of the N-phenylcarbamate (I) to plant pathogenic fungi. It further provides novel N-phenylcarbamates which are representable by the formula (I) wherein X, Y, Z, $R^1$ and $R^2$ are each as defined above, with the provisos that when all the symbols X, Y and —$OR^1$ have the same meanings and are methoxy or ethoxy groups and Z is an oxygen atom, $R^2$ cannot be an ethyl group and that when X and Y are each a bromine atom, —$OR^1$ is a methoxy group and Z is an oxygen atom, $R^2$ cannot be a propargyl group. It furthermore provides a process for producing the novel N-phenylcarbamates (I), which comprises reacting a 3,4,5-trisubstituted aniline of the formula:

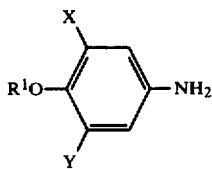

wherein X, Y and $R^1$ are each as defined above, with a chloroformate of the formula:

wherein Z and $R^2$ are each as defined above (Procedure (a)), or reacting a 3,4,5-trisubstituted phenyl isocyanate of the formula:

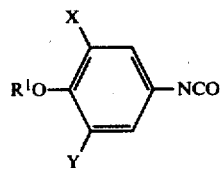

wherein X, Y and $R^1$ are each as defined above, with an alcohol or thiol of the formula:

wherein Z and $R^2$ are each as defined above (Procedure (b)). Moreover, it provides a process for producing the N-phenylcarbamates of the formula (I) wherein at least one of X and Y is a hydroxyiminomethyl group or a lower alkoxyiminomethyl group, which comprises reacting a benzaldehyde of the formula:

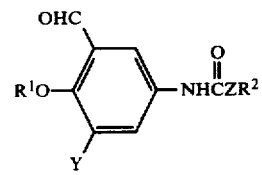

wherein Y, Z, $R^1$ and $R^2$ are each as defined above, with hydroxyamine or lower alkoxyamine (Procedure (c)).

The term "lower" used above and hereinafter in connection with organic radicals or compounds indicates that such radicals or compounds each have not more than 6 carbon atoms. Preferable X and Y are fluorine, chlorine, bromine, iodine, methyl, ethyl, n-propyl, n-butyl, vinyl, 1-propenyl, 2-propenyl, ethynyl, methoxy, ethoxy, cyano, 1,2-dibromoethyl, hydroxymethyl, cyanomethyl, 2-cyanoethyl, 2-cyanovinyl, methoxymethyl, ethoxymethyl, allyloxymethyl, propargyloxymethyl, 2-fluoroethoxymethyl, methoxycarbonyl, ethoxycarbonyl, allyloxycarbonyl, 2-fluoroethoxycarbonyl, propargyloxycarbonyl, dimethoxymethyl, diethoxymethyl, ethylenedioxymethyl, formyl, acetyl, hydroxyiminomethyl, methoxyiminomethyl, carbamoyl or N-methylcarbamoyl. Particularly preferable X and Y are chlorine, bromine, iodine, methyl, ethyl, n-propyl, vinyl, 1-propenyl, 2-propenyl, ethynyl, methoxy, ethoxy, cyano, 1,2-dibromoethyl, methoxymethyl, methoxycarbonyl, dimethoxymethyl, diethoxymethyl, acetyl or methoxyiminomethyl. Especially active are those compounds wherein X and Y are each chlorine, bromine, methoxymethyl, methyl, ethyl or n-propyl, and those compounds wherein X is methoxy or ethoxy and Y is chlorine, bromine, methyl, ethyl, n-propyl, methoxy, ethoxy, cyano, methoxymethyl, methoxycarbonyl, dimethoxymethyl or acetyl. Preferred Z is oxygen. Preferable $R^1$ is methyl, ethyl, n-propyl, allyl, 2-butenyl, 3-butenyl, propargyl, 3-butynyl, difluoromethyl, 2-chloroethyl, 2,2,2-trifluoroethyl, 2-methoxyethyl or cyclopropylmethyl. Particularly preferable $R^1$ is methyl, ethyl, allyl, propargyl, difluoromethyl or 2-chloroethyl. Most preferable $R^1$ is ethyl, allyl, propargyl or 2-chloroethyl. Preferable $R^2$ is methyl, ethyl, isopropyl, sec-butyl, allyl, 1-ethylpropyl, 1-methylbutyl, 1-methylpentyl, 1-methylheptyl, 1-methyl-2-propenyl, propargyl, 2-butenyl, 1-methyl-3-butenyl, 1-pentyl-2-propenyl, 1-methyl-2-propynyl, 1-ethyl-2-propynyl, 2-butynyl, 3-butynyl, 1-methyl-3-butynyl, 1-butyl-2-propynyl, 1-pentyl-2-propynyl, cyclobutyl, 2-cyanoethyl, 2-fluoroethyl, 2-chloroethyl, 2-bromoethyl, 2,2,2-trifluoroethyl, 1-fluoromethyl-2-fluoroethyl, 1-chloromethylethyl, 1-bromomethylpropyl, 1-methoxymethyl-2-chloroethyl, 4-chloro-2-butenyl, 4-chloro-2-butynyl, 1-cyclopropylethyl, 1-cyclopentylethyl, 2-methoxyethyl, 2-n-propoxyethyl, 2-isopropoxyethyl, 2-allyloxyethyl, 2-(2-chloroethoxy)ethyl, 2-benzyloxyethyl, 1-methyl-2-methoxyethyl, 1-methyl-2-n-butoxyethyl or 1-methyl-2-phenoxyethyl. Particularly preferable $R^2$ is methyl, ethyl, isopropyl, sec-butyl, 1-ethylpropyl, allyl, 1-methyl-2-propenyl, 2-butenyl, propargyl, 1-methyl-2-propynyl, 1-ethyl-2-propynyl, 2-butynyl, 1-methyl-3-butynyl, 2-cyanoethyl, 2-fluoroethyl, 1-fluoromethyl-2-fluoroethyl, 1-chloromethylethyl, 1-methoxymethyl-2-chloroethyl, 4-chloro-2-butynyl, 1-cyclopropylethyl, 2-(2-chloroethoxy)ethyl, 1-methyl-2-methoxyethyl or 1-methyl-2-n-butoxyethyl. Most preferable $R^2$ is methyl, ethyl, isopropyl, sec-butyl, allyl, 1-methyl-2-propenyl, 1-methyl-2-propynyl, propargyl, 2-butynyl, 2-cyanoethyl, 4-chloro-2-butynyl or 1-methyl-2-methoxyethyl.

The N-phenylcarbamates (I) are fungicidally effective against a wide scope of plant pathogenic fungi, of which examples are as follows: *Podosphaera leucotricha, Venturia inaequalis, Mycosphaerella pomi, Marssonina mali* and *Sclerotinia mali* of apple, *Phyllactinia kakicola* and *Gloeosporium kaki* of persimmon, *Cladosporium* carpophilum and Phomopsis sp. of peach, *Cercospora viticola, Uncinula necator, Elsinoe ampelina* and *Glomerella cingulata* of grape, *Cercospora beticola* of sugarbeet, *Cercospora arachidicola* and *Cercospora personata* of peanut, *Erysiphe graminis* f. sp. *hordei, Cercosporella herpotrichoides* and *Fusarium nivale* of barley, *Erysiphe graminis* f. sp. *tritici* of wheat, *Sphaerotheca fuliginea* and *Cladosporium cucumerinum* of cucumber, *Cladosporium fulvum* of tomato, *Corynespora melongenae* of eggplant, *Sphaerotheca humuli, Fusarium oxysporum* f. sp. *fragariae* of strawberry, *Botrytis alli* of onion, *Cercospora apii* of cerely, *Phaeoisariopsis griseola* of kidney bean, *Erysiphe cichoracearum* of tobacco, *Diplocarpon rosae* of rose, *Elsinoe fawcetti, Penicillium italicum, Penicillium digitatum* of orange, *Botrytis cinerea* of cucumber, eggplant, tomato, strawberry, pimiento, onion, lettuce, grape, orange, cyclamen, rose or hop, *Sclerotinia sclerotiorum* of cucumber, eggplant, pimiento, lettuce, celery, kidney bean, soybean, azuki bean, potato or sunflower, *Sclerotinia cinerea* of peach or cherry, *Mycosphaerella melonis* of cucumber or melon, etc. Namely, the N-phenylcarbamates (I) are highly effective in controlling the drug-resistant strains of said fungi.

The N-phenylcarbamates (I) are also fungicidally effective against fungi sensitive to said known fungicides as well as fungi to which said known fungicides are ineffective. Examples of such fungi are *Pyricularia oryzae, Pseudoperonospora cubensis, Plasmopara viticola, Phytophthora infestans*, etc.

Advantageously, the N-phenylcarbamates have low toxicity and have little detrimental action on mammals, fish and so on. Also, they may be applied to an agricultural field without causing any material toxicity to important crop plants.

In view of their excellent fungicidal properties, particularly useful are the compounds of the formula (I) wherein X and Y are independently fluorine, chlorine, bromine, iodine, methyl, ethyl, n-propyl, n-butyl, vinyl, 1-propenyl, 2-propenyl, ethynyl, methoxy, ethoxy, cyano, 1,2-dibromoethyl, hydroxymethyl, cyanomethyl, 2-cyanoethyl, 2-cyanovinyl, methoxymethyl, ethoxymethyl, allyloxymethyl, propargyloxymethyl, 2-fluoroethoxymethyl, methoxycarbonyl, ethoxycarbonyl, allyloxycarbonyl, 2-fluoroethoxycarbonyl, propargyloxycarbonyl, dimethoxymethyl, diethoxymethyl, ethylenedioxymethyl, formyl, acetyl, hydroxyiminomethyl, methoxyiminomethyl, carbamoyl or N-methylcarbamoyl, Z is oxygen or sulfur, $R^1$ is methyl, ethyl, n-propyl, allyl, 2-butenyl, 3-butenyl, propargyl, 3-butynyl, difluoromethyl, 2-chloroethyl, 2,2,2-trifluoroethyl, 2-methoxyethyl or cyclopropylmethyl, $R^2$ is methyl, ethyl, isopropyl, sec-butyl, allyl, 1-ethylpropyl, 1-methylbutyl, 1-methylpentyl, 1-methylheptyl, 1-methyl-2-propenyl, propargyl, 2-butenyl, 1-methyl-3-butenyl, 1-pentyl-2-propenyl, 1-methyl-2-propynyl, 1-ethyl-2-propynyl, 2-butynyl, 3-butynyl, 1-methyl-3-butynyl, 1-butyl-2-propynyl, 1-pentyl-2-propynyl, cyclobutyl, 2-cyanoethyl, 2-fluoroethyl, 2-chloroethyl, 2-bromoethyl, 2,2,2-trifluoroethyl, 1-fluoromethyl-2-fluoroethyl, 1-chloromethylethyl, 1-bromomethylpropyl, 1-methoxymethyl-2-chloroethyl, 4-chloro-2-butenyl, 4-chloro-2-butynyl, 1-cyclopropylethyl, 1-cyclopentylethyl, 2-methoxyethyl, 2-n-propoxyethyl, 2-isopropoxyethyl, 2-allyloxyethyl, 2-(2-chloroethoxy)ethyl, 2-benzyloxyethyl, 1-methyl-2-methoxyethyl, 1-methyl-2-n-butoxyethyl or 1-methyl-2-phenoxyethyl. Preferred are the compounds of the formula (I) wherein X and Y are independently chlorine, bromine, iodine, methyl, ethyl, n-propyl, vinyl, 1-propenyl, 2-propenyl, ethynyl, methoxy, ethoxy, cyano, 1,2-dibromoethyl, methoxymethyl, methoxycarbonyl, dimethoxymethyl, diethoxymethyl, acetyl or methoxyiminomethyl, Z is oxygen, $R^1$ is methyl, ethyl, allyl, propargyl, difluoromethyl or 2-chloroethyl, $R^2$ is methyl, ethyl, isopropyl, sec-butyl, allyl, 1-ethylpropyl, 1-methyl-2-propenyl, 2-butenyl, propargyl, 1-methyl-2-propynyl, 1-ethyl-2-propynyl, 2-butynyl, 1-methyl-3-butynyl, 2-cyanoethyl, 2-fluoroethyl, 1-fluoromethyl-2-fluoroethyl, 1-chloromethylethyl, 1-methoxymethyl-2-chloroethyl, 4-chloro-2-butynyl, 1-cyclopropylethyl, 2-(2-chloroethoxy)ethyl, 1-methyl-2-methoxyethyl or 1-methyl2-n-butoxyethyl.

Particularly preferred are the compounds of the formula (I) wherein X and Y are each chlorine, bromine, methoxymethyl, methyl, ethyl or n-propyl, Z is oxygen, $R^1$ is ethyl, allyl, propargyl or 2-chloroethyl and $R^2$ is methyl, ethyl, isopropyl, sec-butyl, allyl, 1-methyl-2-propenyl, propargyl, 1-methyl-2-propynyl, 2-butynyl, 2-cyanoethyl, 4-chloro-2-butynyl or 1-methyl-2-methoxyethyl and the compounds of the formula (I) wherein X is methoxy or ethoxy, Y is chlorine, bromine, methyl, ethyl, n-propyl, methoxy, ethoxy, cyano, methoxymethyl, methoxycarbonyl, dimethoxymethyl or acetyl, Z is oxygen, $R^1$ is ethyl, allyl, propargyl or 2-chloroethyl and $R^2$ is methyl, ethyl, isopropyl, sec-butyl, allyl, 1-methyl-2-propenyl, propargyl, 1-methyl-2-propynyl, 2-butynyl, 2-cyanoethyl, 4-chloro-2-butynyl or 1-methyl-2-methoxyethyl.

More preferred are the compounds of the formula (I) wherein X and Y are each chlorine, methyl or methoxymethyl, Z is oxygen, $R^1$ is ethyl, allyl, propargyl or 2-chloroethyl, preferably ethyl, and $R^2$ is methyl, ethyl, isopropyl, sec-butyl, allyl, 1-methyl-2-propenyl, propargyl, 1-methyl-2-propynyl, 2-butynyl, 2-cyanoethyl, 4-chloro-2-butynyl or 1-methyl-2-methoxyethyl and the compounds of the formula (I) wherein X is methoxy or ethoxy, Y is chlorine, methyl, methoxymethyl or cyano, Z is oxygen, $R^1$ is ethyl, allyl, propargyl or 2-chloroethyl, preferably ethyl, and $R^2$ is methyl, ethyl, isopropyl, sec-butyl, allyl, 1-methyl-2-propenyl, propargyl, 1-methyl-2-propynyl, 2-butynyl, 2-cyanoethyl, 4-chloro-2-butynyl or 1-methyl-2-methoxyethyl. Most preferred are the following:

Isopropyl N-(3,5-dichloro-4-ethoxyphenyl)carbamate;
Isopropyl N-(3,5-dimethyl-4-ethoxyphenyl)carbamate;
Propargyl N-(3,5-dimethyl-4-ethoxyphenyl)carbamate;
1-Methyl-2-propenyl N-(3,5-dimethyl-4-ethoxyphenyl)carbamate;
1-Methyl-2-propynyl N-(3,5-dimethyl-4-ethoxyphenyl)carbamate;
1-Methyl-2-methoxyethyl N-( 3,5-dimethyl-4-ethoxyphenyl)carbamate;
Isopropyl N-[3,5-dimethyl-4-(2-propynyloxy)phenyl]carbamate;
Isopropyl N-(3-chloro-4-ethoxy-5-methoxyphenyl)carbamate;
Methyl N-(3-chloro-4,5-diethoxyphenyl)carbamate;
Ethyl N-(3-chloro-4,5-diethoxyphenyl)carbamate;
Isopropyl N-(3-chloro-4,5-diethoxyphenyl)carbamate;
sec-Butyl N-(3-chloro-4,5-diethoxyphenyl)carbamate;
Allyl N-(3-chloro-4,5-diethoxyphenyl)carbamate;
Propargyl N-(3-chloro-4,5-diethoxyphenyl)carbamate;
1-Methyl-2-propenyl N-(3-chloro-4,5-diethoxyphenyl)carbamate;
1-Methyl-2-propynyl N-(3-chloro-4,5-diethoxyphenyl)carbamate;

4-Chloro-2-butynyl N-(3-chloro-4,5-diethoxyphenyl)-carbamate;
2-Cyanoethyl N-(3-chloro-4,5-diethoxyphenyl)carbamate;
Isopropyl N-[3-chloro-5-ethoxy-4-(2-propenyloxy)phenyl]carbamate;
1-Methyl-2-methoxyethyl N-[3-chloro-5-ethoxy-4-(2-propenyloxy)phenyl]carbamate;
Isopropyl N-[3-chloro-5-ethoxy-4-(2-propynyloxy)phenyl]carbamate;
Isopropyl N-[3-chloro-4-(2-chloroethyloxy)-5-ethoxyphenyl]carbamate;
Isopropyl N-(3-methoxy-4-ethoxy-5-methylphenyl)carbamate;
Methyl N-(3,4-diethoxy-5-methylphenyl)carbamate;
Ethyl N-(3,4-diethoxy-5-methylphenyl)carbamate;
Isopropyl N-(3,4-diethoxy-5-methylphenyl)carbamate;
sec-Butyl N-(3,4-diethoxy-5-methylphenyl)carbamate;
Propargyl N-(3,4-diethoxy-5-methylphenyl)carbamate;
1-Methyl-2-propenyl N-(3,4-diethoxy-5-methylphenyl)carbamate;
1-Methyl-2-propynyl N-(3,4-diethoxy-5-methylphenyl)carbamate;
1-Methyl-2-methoxyethyl N-(3,4-diethoxy-5-methylphenyl)carbamate;
4-Chloro-2-butynyl N-(3,4-diethoxy-5-methylphenyl)carbamate;
Isopropyl N-(3,4-diethoxy-5-ethylphenyl)carbamate;
Isopropyl N-(3,4-diethoxy-5-vinylphenyl)carbamate;
Isopropyl N-(3,4-diethoxy-5-methoxyphenyl)carbamate;
Isopropyl N-(3,4-diethoxy-5-methoxymethylphenyl)carbamate;
1-Methyl-2-methoxyethyl N-(3,4-diethoxy-5-methoxymethylphenyl)carbamate;
Isopropyl N-(3-chloro-4-ethoxy-5-methoxymethylphenyl)carbamate;
Isopropyl N-(3,4-diethoxy-5-methoxycarbonylphenyl)carbamate;
Isopropyl N-(3-cyano-4,5-diethoxyphenyl)carbamate;
Isopropyl N-(3-methyl-4-ethoxy-5-methoxymethylphenyl)carbamate;
Isopropyl N-(3-methyl-4-ethoxy-5-n-propylphenyl)carbamate;
Isopropyl N-(3,4-diethoxy-5-bromophenyl)carbamate;
Isopropyl N-(3-methyl-4-propynyloxy-5-ethoxyphenyl)carbamate;
Isopropyl N-(3,4-diethoxy-5-acetylphenyl)carbamate;
Isopropyl N-[3,4-diethoxy-5-(1,2-dibromoethyl)phenyl]carbamate;
Isopropyl N-(3-chloro-4-propynyloxy-5-methoxyphenyl)carbamate;
Isopropyl N-(3,4-diethoxy-5-dimethoxymethylphenyl)carbamate;
Isopropyl N-(3-chloro-4-ethoxy-5-n-propylphenyl)carbamate;
Isopropyl N-(3-bromo-4-ethoxy-5-methoxyphenyl)carbamate;
Isopropyl N-(3,5-diethyl-4-ethoxyphenyl)carbamate;
Isopropyl N-(3-chloro-4-ethoxy-5-methylphenyl)carbamate;
Isopropyl N-(3-methyl-4-ethoxy-5-allylphenyl)carbamate, etc.

The N-phenylcarbamates (I) can be prepared by either one of the following procedures:

Procedure (a):

Reaction of the 3,4,5-trisubstituted aniline (II) with the chloroformate (III).

The reaction is usually carried out in the presence of an inert solvent (e.g. benzene, toluene, xylene, diethyl ether, tetrahydrofuran, dioxane, chloroform, carbon tetrachloride, ethyl acetate, pyridine, dimethylformamide). When desired, the reaction may be performed in the existence of a dehydrohalogenating agent (e.g. pyridine, triethylamine, diethylaniline, sodium hydroxide, potassium hydroxide) so as to obtain the objective compound (I) in a high yield. The reaction may be accomplished at a temperature of 0° to 150° C. instantaneously or within 12 hours.

Procedure (b):

Reaction of the 3,4,5-trisubstituted phenyl isocyanate (IV) with the alcohol or thiol (V).

The reaction is usually carried out in the absence or presence of an inert solvent (e.g. benzene, toluene, xylene, diethyl ether, tetrahydrofuran, dioxane, N,N-dimethylformamide, chloroform, carbon tetrachloride). When desired, a catalyst (e.g. triethylamine, diethylaniline, 1,4-diazabicyclo(2,2,2)octane) may be used. The reaction is normally accomplished at a temperature of 0° to 50° C. instantaneously or within 12 hours.

In case of the N-phenylcarbamates of the formula (I) wherein at least one of X and Y is a hydroxyiminomethyl group or a lower alkoxyiminomethyl group, it may be prepared by the following procedure (Procedure (c)): reacting the benzaldehyde (VI) with an equimolar or excess amount of hydroxylamine or lower alkoxyamine in an inert solvent (e.g. methanol, ethanol). The reaction may be brought to completion in about 0.5 to 12 hours. For preparation of the N-phenylcarbamates of the formula (I) wherein both of X and Y are hydroxyiminomethyl groups or lower alkoxyiminomethyl groups, there may be used as the starting material the benzaldehyde of the formula (VI) wherein Y is a formyl group.

The 3,4,5-trisubstituted aniline (II) used as the starting material in Procedure (a) can be prepared by reducing a nitrobenzene of the formula:

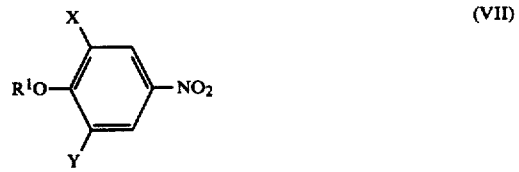
(VII)

wherein X, Y and $R^1$ are each as defined above, which is obtainable by reacting a nitrophenol of the formula:

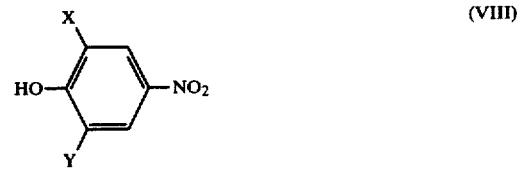
(VIII)

wherein X and Y are each as defined above with a reagent of the formula: $A-R^1$ wherein A is a tosyloxy or mesyloxy group or a halogen atom and $R^1$ is as defined above.

The reaction of the nitrophenol (VIII) with the reagent may be carried out in an inert solvent such as water, benzene, toluene, xylene, diethyl ether, tetrahydrofuran, dioxane, chloroform, tetrachloromethane, ethyl acetate, ethanol, isopropanol or dimethylformamide, when desired, in the presence of a base such as pyridine, triethylamine, sodium hydroxide, potassium hydroxide or sodium carbonate. If necessary, the reaction mass may be heated or cooled. The reaction may be accomplished within 0.5 to 12 hours to give the objective compound in a high yield.

The reduction of the nitrobenzene (VII) is usually carried out by a conventional reduction technique such as catalytic reduction with platinum oxide, Raney nickel, platinum black or palladium on carbon, reduction in acidic media, for example, in water containing hydrogen chloride, sulfuric acid or acetic acid, using tin, stannous chloride or iron, or reduction in basic media, for example, in methanol or ethanol, using sodium sulfide or sodium hydrosulfide.

The nitrophenol (VIII) can be prepared by a known method [Bavin and Scott: Can. J. Chem., 36, 1284 (1958)].

The 3,4,5-trisubstituted phenyl isocyanate (IV) employed as the starting material in Procedure (b) may be prepared by reacting the 3,4,5-trisubstituted aniline (II) with phosgene. This reaction is usually carried out in the presence of an inert solvent (e.g. benzene, toluene, xylene, ethyl acetate) at a temperature of 50° C. to the refluxing temperature of the solvent. The reaction may be accomplished instantaneously or within 12 hours.

The procedures for preparation of N-phenylcarbamates (I) are illustratively shown in the following Examples.

EXAMPLE 1

Preparation of isopropy N-(3,5-dichloro-4-methoxyphenyl)carbamate according to Procedure (a):

3,5-Dichloro-4-methoxyaniline (1.8 g) and diethylaniline (1.5 g) were dissolved in benzene (20 ml). To the resultant solution was dropwise added isopropyl chloroformate (1.2 g) in 5 minutes under ice-cooling. After being allowed to stand at room temperature for 12 hours, the reaction mixture was poured into ice water and extracted with ethyl acetate. The extract was washed with water, dried over magnesium sulfate and concentrated under reduced pressure. The residue was purified by silica gel chromatography using a mixture of benzene and tetrahydrofuran as the eluent to give isopropyl N-(3,5-dichloro-4-methoxyphenyl)carbamate (Compound No. 2) (2.4 g) in a yield of 91.8%.

M.P., 107.5°–108° C.

Elementary analysis: Calcd. for $C_{11}H_{13}Cl_2NO_3$: N, 5.02%; C, 47.38%; H, 4.69%; Cl, 25.44%. Found: N, 5.11%; C, 47.52%; H, 4.76%. Cl, 25.49%.

EXAMPLE 2

Preparation of isopropyl N-(3-bromo-5-chloro-4-methoxyphenyl)carbamate according to Procedure (b):

A mixture of 3-bromo-5-chloro-4-methoxyaniline (13.0 g) in toluene (100 ml) was dropwise added to a toluene solution containing 20 g of phosgene at 10° to 20° C. The resulting mixture was gradually heated and, after being refluxed for 30 minutes, cooled to room temperature. The solvent was removed by distillation under reduced pressure to give 3-bromo-5-chloro-4-methoxyphenyl isocyanate (14.4 g). The thus obtained crude substance was added to an isopropanol solution (50 ml) containing triethylamine (1 g). The resultant mixture was allowed to stand at room temperature for 12 hours, poured into ice-water and extracted with ethyl acetate. The extract was washed with water, dried over magnesium sulfate and concentrated under reduced pressure. The residue was purified by silica gel chromatography using a mixture of benzene and tetrahydrofuran as the eluent to give isopropyl N-(3-bromo-5-chloro-4-methoxyphenyl)carbamate (Compound No. 33) (16.4 g) in a yield of 92% (calculated from the starting 3-bromo-5-chloro-4-methoxyaniline).

M.P., 112–113.5° C.

Elementary analysis: Calcd. for $C_{11}H_{13}NO_3BrCl$: N, 4.33%; C, 40.87%;, H, 4.05%; Br, 24.72%, Cl, 10.97%. Found: N, 4.35%, C, 40.84%; H, 3.91%; Br, 25.06%; Cl, 11.20%.

EXAMPLE 3

Preparation of isopropyl N-(3-ethyl-4-ethoxy-5-chlorophenyl)carbamate according to Procedure (a):

3-Ethyl-4-ethoxy-5-chloroanilie (1.9 g) and diethylaniline (1.5 g) were dissolved in toluene (20 ml). To the resultant solution was dropwise added isopropyl chloroformate (1.2 g) in 5 minutes under ice-cooling. After being allowed to stand at room temperature for 12 hours, the reaction mixture was poured into ice water and extracted with toluene. The extract was washed with water, dried over magnesium sulfate and concentrated under reduced pressure. The residue was purified by silica gel chromatography using toluene as the eluent to give isopropyl N-(3-ethyl-4-ethoxy-5-chlorophenyl)-carbamate (Compound No. 53) (2.4 g) in a yield of 89%. M.P., 79°–80.5° C.

Elementary analysis: Calcd. for $C_{14}H_{20}NO_3Cl$: N, 4.89%; C, 58.69%; H, 7.04%; Cl, 12.38%. Found: N, 4.88%; C, 58.43%; H, 6.97%; Cl, 12.28%.

EXAMPLE 4

Preparation of isopropyl N-(3-ethyl-4-ethoxy-5-methylphenyl)carbamate according to Procedure (b):

A mixture of 3-ethyl-4-ethoxy-5-methylaniline (1.8 g) in toluene (20 ml was dropwise added to a toluene solution containing 10 g of phosgene at 10° to 20° C. The resulting mixture was gradually heated and, after being refluxed for 30 minutes, cooled to room temperature. The solvent was removed by distillation under reduced pressure to give 3-ethyl-4-ethoxy-5-methylphenyl isocyanate (2.1 g). The thus obtained crude substance was added to an isopropanol solution (20 ml) containing triethylamine (1 g). The resultant mixture was allowed to stand at room temperature for 12 hours, poured into ice-water and extracted with toluene. The extract was washed with water, dried over magnesium sulfate and concentrated under reduced pressure. The residue was purified by silica gel chromatography using toluene as the eluent to give isopropyl N-(3-ethyl-4-ethoxy-5-methylphenyl)carbamate (Compound No. 93) ((2.4 g) in a yield of 91% (calculated from the starting 3-ethyl-4-ethoxy-5-methylaniline). M.P., 68°–69.5° C.

Elementaly analysis: Calcd. for $C_{15}H_{23}NO_3$: N, 5.28%; C, 67.89%; H, 8.74%. Found: N, 5.21%; C, 67.85%; H, 8.96%.

EXAMPLE 5

Preparation of isopropyl N-(3,4-diethoxy-5-methoxyiminomethylphenyl)carbamate according to Procedure (c):

Isopropyl N-(3,4-diethoxy-5-formylphenyl)carbamate (0.6 g) was dissolved in ethanol (20 ml). To the solution was added an aqueous solution (10 ml) containing sodium hydroxide (0.32 g) and methoxyamine hydrochloride (0.66 g). After being allowed to stand for 12 hours, the reaction mixture was concentrated in vacuo, and the residue was dissolved in ethyl acetate. The resultant solution was washed with water, dried over magnesium sulfate and concentrated under reduced pressure. The residue was washed with hexane to give isopropyl N-(3,4-diethoxy-5-methoxyiminomethylphenyl)carbamate (Compound No. 191) (0.61 g) in a yield of 93%. M.P., 110°–111.5° C.

Elementary analysis: Calcd. for $C_{16}H_{24}N_2O_5$: C, 59.24%; H, 7.46%; N, 8.64%. Found: C, 59.01%, H, 7.56%; N, 8.34%.

According to either one of the above Procedures (a), (b) or (c), the N-phenylcarbamates of the formula (I) as shown in Table 1 can be prepared:

TABLE 1

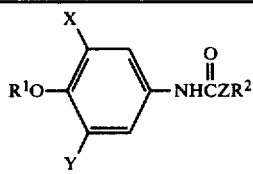

| Compound No. | X | Y | R$^1$ | R$^2$ | Z | Physical constant |
|---|---|---|---|---|---|---|
| 1 | —Cl | —Cl | —CH$_3$ | —C$_2$H$_5$ | O | M.P. 94–95.5° C. |
| 2 | —Cl | —Cl | —CH$_3$ | —CH(CH$_3$)$_2$ | O | M.P. 107.5–108° C. |
| 3 | —Cl | —Cl | —CH$_3$ | —CH(CH$_3$)(C$_2$H$_5$) | O | M.P. 75.5–76° C. |
| 4 | —Cl | —Cl | —CH$_3$ | —CH(C$_2$H$_5$)$_2$ | O | M.P. 85–86.5° C. |
| 5 | —Cl | —Cl | —CH$_3$ | —CH$_2$C≡CH | O | M.P. 123–124.5° C. |
| 6 | —Cl | —Cl | —CH$_3$ | —CH(CH$_3$)—CH=CH$_2$ | O | M.P. 57–58° C. |
| 7 | —Cl | —Cl | —CH$_3$ | —CH(CH$_3$)—C≡CH | O | M.P. 72–73° C. |
| 8 | —Cl | —Cl | —CH$_3$ | —CH(C$_2$H$_5$)—C≡CH | O | M.P. 61–62° C. |
| 9 | —Cl | —Cl | —CH$_3$ | —CH$_2$CH=CHCH$_3$ | O | M.P. 75–76° C. |
| 10 | —Cl | —Cl | —CH$_3$ | —CH$_2$C≡CCH$_3$ | O | M.P. 110–111° C. |
| 11 | —Cl | —Cl | —CH$_3$ | —CH$_2$CH$_2$Cl | O | $n_D^{24.5}$ 1.5541 |
| 12 | —Cl | —Cl | —CH$_3$ | —CH$_2$CH=CHCH$_2$Cl | O | $n_D^{22.0}$ 1.5641 |
| 13 | —Cl | —Cl | —CH$_3$ | —CH$_2$—C≡C—CH$_2$Cl | O | M.P. 105.5–106.5° C. |
| 14 | —Cl | —Cl | —CH$_3$ | —CH(CH$_3$)—CH(CH$_2$CH$_2$) (cyclopropyl) | O | $n_D^{23.0}$ 1.5330 |
| 15 | —Cl | —Cl | —C$_2$H$_5$ | —CH(CH$_3$)$_2$ | O | M.P. 65–65.5° C. |
| 16 | —Cl | —Cl | —C$_2$H$_5$ | —CH$_2$CH$_2$OCH$_3$ | O | M.P. 90–91° C. |
| 17 | —Cl | —Cl | —C$_2$H$_5$ | —CH$_2$CH$_2$O(n)C$_3$H$_7$ | O | $n_D^{24.5}$ 1.5302 |
| 18 | —Cl | —Cl | —C$_2$H$_5$ | —CH$_2$CH$_2$OCH(CH$_3$)$_2$ | O | $n_D^{24.5}$ 1.5288 |

TABLE 1-continued $$\text{R}^1\text{O}\underset{Y}{\overset{X}{\bigcirc}}\text{NHCZR}^2$$

| Compound No. | X | Y | R¹ | R² | Z | Physical constant |
|---|---|---|---|---|---|---|
| 19 | —Cl | —Cl | —CH₂CH₂CH₃ | —CH(CH₃)₂ | O | $n_D^{24.5}$ 1.5251 |
| 20 | —Cl | —Cl | —CH₂CH=CH₂ | —CH(CH₃)₂ | O | $n_D^{20.5}$ 1.5439 |
| 21 | —Cl | —Cl | —CH₂CH₂OCH₃ | —CH(CH₃)₂ | O | $n_D^{20.5}$ 1.5283 |
| 22 | —Cl | —Cl | —CH₂C≡CH | —CH(CH₃)₂ | O | $n_D^{20.5}$ 1.5511 |
| 23 | —Cl | —Cl | —CH₂CH₂CH=CH₂ | —CH(CH₃)₂ | O | $n_D^{21.3}$ 1.5312 |
| 24 | —Cl | —Cl | —CH₂CH₂C≡CH | —CH(CH₃)₂ | O | $n_D^{21.5}$ 1.5220 |
| 25 | —Cl | —Cl | —CH₂CH(cyclopropyl) | —CH(CH₃)₂ | O | $n_D^{20.5}$ 1.5429 |
| 26 | —Cl | —Cl | —CHF₂ | —CH₃ | O | M.P. 100-101° C. |
| 27 | —Cl | —Cl | —CHF₂ | —C₂H₅ | O | M.P. 72-73° C. |
| 28 | —Cl | —Cl | —CHF₂ | —CH(CH₃)₂ | O | M.P. 131-132° C. |
| 29 | —Cl | —Cl | —CHF₂ | —CH(CH₃)—C≡CH | O | M.P. 118-119° C. |
| 30 | —Cl | —Cl | —CHF₂ | —CH(C₂H₅)—C≡CH | O | M.P. 114-115° C. |
| 31 | —Cl | —Cl | —CHF₂ | —CH₂C≡CCH₂Cl | O | M.P. 83.5-84.5° C. |
| 32 | —Cl | —Cl | —CH₂CF₃ | —CH(CH₃)₂ | O | M.P. 133-135° C. |
| 33 | —Cl | —Br | —CH₃ | —CH(CH₃)₂ | O | M.P. 112-113.5° C. |

TABLE 1-continued structure: R¹O-(phenyl with X, Y substituents)-NHC(=O)ZR²

| Compound No. | X | Y | R¹ | R² | Z | Physical constant |
|---|---|---|---|---|---|---|
| 34 | —Br | —Br | —CH₃ | —CH₃ | O | M.P. 111–112° C. |
| 35 | —Br | —Br | —CH₃ | —C₂H₅ | O | M.P. 109.5–111° C. |
| 36 | —Br | —Br | —CH₃ | —CH(CH₃)₂ | O | M.P. 122.5–124° C. |
| 37 | —Br | —Br | —CH₃ | —CH₂C≡CH | O | M.P. 114.5–115° C. |
| 38 | —Br | —Br | —CH₃ | —CH(CH₃)—CH=CH₂ | O | M.P. 56–57.5° C. |
| 39 | —Br | —Br | —CH₃ | —CH(CH₃)—C≡CH | O | M.P. 78.5–81.5° C. |
| 40 | —Br | —Br | —CH₃ | —CH₂CH=CHCH₃ | O | M.P. 75–76° C. |
| 41 | —Br | —Br | —CH₃ | —CH₂C≡CCH₂Cl | O | M.P. 112.5–113.5° C. |
| 42 | —Br | —Br | —CHF₂ | —CH₃ | O | M.P. 84–85° C. |
| 43 | —Br | —Br | —CHF₂ | —C₂H₅ | O | M.P. 136–137° C. |
| 44 | —Br | —Br | —CHF₂ | —CH(CH₃)₂ | O | M.P. 157–159° C. |
| 45 | —Br | —Br | —CHF₂ | —CH₂C≡CH | O | M.P. 123.5–124.5° C. |
| 46 | —Br | —Br | —CHF₂ | —CH(CH₃)—CH=CH₂ | O | M.P. 135.5–137° C. |
| 47 | —Br | —Br | —CHF₂ | —CH(CH₃)—C≡CH | O | M.P. 140.5–142° C. |
| 48 | —Br | —Br | —CHF₂ | —CH₂CH=CHCH₃ | O | M.P. 95–97.5° C. |
| 49 | —Br | —Br | —CHF₂ | —CH(CH₃)—CH₂Cl | O | M.P. 110–113.5° C. |
| 50 | —Br | —Br | —CHF₂ | —CH₂C≡CCH₂Cl | O | M.P. 105–106° C. |
| 51 | —Cl | —CH₃ | —C₂H₅ | —CH(CH₃)₂ | O | M.P. 79.5–80.5° C. |
| 52 | —Cl | —CH₃ | —CHF₂ | —CH(CH₃)₂ | O | M.P. 94–95° C. |
| 53 | —Cl | —C₂H₅ | —C₂H₅ | —CH(CH₃)₂ | O | M.P. 79–80.5° C. |

TABLE 1-continued $$\underset{Y}{\overset{X}{R^1O-C_6H_3}}-NHCZR^2 \;(\text{with } C=O)$$

| Compound No. | X | Y | R¹ | R² | Z | Physical constant |
|---|---|---|---|---|---|---|
| 54 | —Cl | —CH$_2$CH$_2$CH$_3$ | —C$_2$H$_5$ | —CH(CH$_3$)$_2$ | O | M.P. 71.5–72° C. |
| 55 | —CH$_3$ | —CH$_3$ | —CH$_3$ | —CH(CH$_3$)$_2$ | O | M.P. 89–90° C. |
| 56 | —CH$_3$ | —CH$_3$ | —CH$_3$ | —CH$_2$C≡CCH$_2$Cl | O | M.P. 72–73° C. |
| 57 | —CH$_3$ | —CH$_3$ | —C$_2$H$_5$ | —CH$_3$ | O | M.P. 60–61° C. |
| 58 | —CH$_3$ | —CH$_3$ | —C$_2$H$_5$ | —C$_2$H$_5$ | O | M.P. 49.5–51° C. |
| 59 | —CH$_3$ | —CH$_3$ | —C$_2$H$_5$ | —CH(CH$_3$)$_2$ | O | M.P. 98–99° C. |
| 60 | —CH$_3$ | —CH$_3$ | —C$_2$H$_5$ | —CH(CH$_3$)(C$_2$H$_5$) | O | M.P. 86–87° C. |
| 61 | —CH$_3$ | —CH$_3$ | —C$_2$H$_5$ | —CH(CH$_3$)(CH$_2$CH$_2$CH$_3$) | O | $n_D^{19}$ 1.5101 |
| 62 | —CH$_3$ | —CH$_3$ | —C$_2$H$_5$ | —CH$_2$C≡CH | O | M.P. 110–111° C. |
| 63 | —CH$_3$ | —CH$_3$ | —C$_2$H$_5$ | —CH$_2$CH$_2$C≡CH | O | M.P. 67–68° C. |
| 64 | —CH$_3$ | —CH$_3$ | —C$_2$H$_5$ | —CH(CH$_3$)—CH=CH$_2$ | O | M.P. 83.5–84.5° C. |
| 65 | —CH$_3$ | —CH$_3$ | —C$_2$H$_5$ | —CH(CH$_3$)—C≡CH | O | M.P. 103–104° C. |
| 66 | —CH$_3$ | —CH$_3$ | —C$_2$H$_5$ | —CH(C$_4$H$_9$(n))—C≡CH | O | M.P. 63.5–65° C. |
| 67 | —CH$_3$ | —CH$_3$ | —C$_2$H$_5$ | —CH(CH$_3$)—CH$_2$CH=CH$_2$ | O | M.P. 68.5–69.5° C. |
| 68 | —CH$_3$ | —CH$_3$ | —C$_2$H$_5$ | —CH(CH$_3$)—CH$_2$C≡CH | O | M.P. 75.5–76.5° C. |
| 69 | —CH$_3$ | —CH$_3$ | —C$_2$H$_5$ | —CH$_2$CH$_2$F | O | M.P. 71–72° C. |
| 70 | —CH$_3$ | —CH$_3$ | —C$_2$H$_5$ | —CH(CH$_2$F)$_2$ | O | M.P. 95–96° C. |
| 71 | —CH$_3$ | —CH$_3$ | —C$_2$H$_5$ | —CH(CH$_2$Cl)(CH$_2$OCH$_3$) | O | M.P. 82–83° C. |

TABLE 1-continued

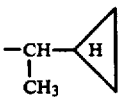

| Compound No. | X | Y | R¹ | R² | Z | Physical constant |
|---|---|---|---|---|---|---|
| 72 | —CH₃ | —CH₃ | —C₂H₅ | —CH₂CH₂OCH₂CH=CH₂ | O | $n_D^{19.5}$ 1.5221 |
| 73 | —CH₃ | —CH₃ | —C₂H₅ | —CH(CH₃)—CH₂OCH₃ | O | $n_D^{22.5}$ 1.5051 |
| 74 | —CH₃ | —CH₃ | —C₂H₅ | —CH(CH₃)-cyclopropyl-H | O | M.P. 82-83° C. |
| 75 | —CH₃ | —CH₃ | —C₂H₅ | —cyclobutyl-H | O | M.P. 124-125° C. |
| 76 | —CH₃ | —CH₃ | —C₂H₅ | —CH₂C≡CCH₂Cl | O | M.P. 107-108° C. |
| 77 | —CH₃ | —CH₃ | —CH₂CH=CH₂ | —CH(CH₃)₂ | O | $n_D^{19.6}$ 1.5228 |
| 78 | —CH₃ | —CH₃ | —CH₂C≡CH | —CH(CH₃)₂ | O | $n_D^{22.5}$ 1.5261 |
| 79 | —CH₃ | —CH₃ | —CHF₂ | —CH(CH₃)₂ | O | M.P. 51-52° C. |
| 80 | —CH₃ | —CH₃ | —CHF₂ | —CH(CH₃)(C₂H₅) | O | $n_D^{22}$ 1.4908 |
| 81 | —CH₃ | —CH₃ | —CHF₂ | —CH(CH₃)—CH=CH₂ | O | $n_D^{22}$ 1.4976 |
| 82 | —CH₃ | —CH₂CH₂CH₃ | —C₂H₅ | —CH(CH₃)₂ | O | $n_D^{18.5}$ 1.5127 |
| 83 | —CH₃ | —CH₂CH=CH₂ | —C₂H₅ | —CH(CH₃)₂ | O | $n_D^{17.5}$ 1.5205 |
| 84 | —Br | —F | —C₂H₅ | —CH(CH₃)₂ | O | $n_D^{20.5}$ 1.5299 |
| 85 | —I | —I | —C₂H₅ | —CH(CH₃)₂ | O | M.P. 107.5-109° C. |

TABLE 1-continued

| Compound No. | X | Y | R¹ | R² | Z | Physical constant |
|---|---|---|---|---|---|---|
| 86 | —CH₃ | —CH₃ | —CHF₂ | —CH(CH₃)—C≡CH | O | M.P. 81–82° C. |
| 87 | —CH₃ | —CH₃ | —CHF₂ | —CH(C₂H₅)—C≡CH | O | M.P. 60–61° C. |
| 88 | —CH₃ | —CH₃ | —CHF₂ | —CH₂C≡CCH₃ | O | M.P. 77–78° C. |
| 89 | —CH₃ | —CH₃ | —CHF₂ | —CH₂CH₂Br | O | M.P. 99.5–100.5° C. |
| 90 | —CH₃ | —CH₃ | —CHF₂ | —CH₂C≡CCH₂Cl | O | M.P. 71–73° C. |
| 91 | —CH₃ | —CH₃ | —CHF₂ | —CH(CH₃)—CH₂OCH₃ | O | M.P. 91–93° C. |
| 92 | —CH₃ | —CH₃ | —CHF₂ | —CH(CH₃)—cyclopropyl | O | $n_D^{24.5}$ 1.4965 |
| 93 | —CH₃ | —C₂H₅ | —C₂H₅ | —CH(CH₃)₂ | O | M.P. 68–69.5 |
| 94 | —CH₃ | —C₂H₅ | —C₂H₅ | —CH₂CH₂F | O | $n_D^{22.9}$ 1.5122 |
| 95 | —CH₃ | —C₂H₅ | —C₂H₅ | —CH₂CF₃ | O | M.P. 80–81.5° C. |
| 96 | —CH₃ | —C₂H₅ | —C₂H₅ | —CH(CH₃)(CH₂Cl) | O | M.P. 66–68° C. |
| 97 | —CH₃ | —C₂H₅ | —C₂H₅ | —CH(CH₂OCH₃)(CH₂Cl) | O | $n_D^{22.9}$ 1.5149 |
| 98 | —CH₃ | —C₂H₅ | —CH₂CH₂CH₃ | —CH(C₂H₅)₂ | O | M.P. 68–71° C. |
| 99 | —CH₃ | —C₂H₅ | —CH₂CH₂CH₃ | —CH₂C≡CH | O | $n_D^{24.6}$ 1.5280 |
| 100 | —CH₃ | —C₂H₅ | —CH₂CH=CH₂ | —CH₂CH=CHCH₂Cl | O | $n_D^{25.0}$ 1.5335 |
| 101 | —CH₃ | —C₂H₅ | —CH₂C≡CH | —CH(CH₃)(C₂H₅) | O | $n_D^{24.5}$ 1.5235 |
| 102 | —CH₃ | —C₂H₅ | —CH₂CH₂CH=CH₂ | —CH(C₂H₅)—C≡CH | O | $n_D^{23.5}$ 1.5225 |
| 103 | —CH₃ | —C₂H₅ | —CH₂CH(cyclopropyl) | —CH(CH₃)₂ | O | $n_D^{24.6}$ 1.5262 |
| 104 | —C₂H₅ | —C₂H₅ | —C₂H₅ | —CH₃ | O | M.P. 83.5–85° C. |

TABLE 1-continued $$\text{R}^1\text{O}-\underset{Y}{\overset{X}{\bigcirc}}-\text{NHCZR}^2 \quad (Z=\overset{O}{\|})$$

| Compound No. | X | Y | R¹ | R² | Z | Physical constant |
|---|---|---|---|---|---|---|
| 105 | —C₂H₅ | —C₂H₅ | —C₂H₅ | —CH(CH₃)₂ | O | M.P. 87–89.5° C. |
| 106 | —C₂H₅ | —C₂H₅ | —C₂H₅ | —CH₂C≡CCH₂Cl | O | M.P. 84–86.5° C. |
| 107 | —C₂H₅ | —C₂H₅ | —CH₂CH₂C≡CH | —CH(CH₃)—CH≡CH | O | $n_D^{23.5}$ 1.5335 |
| 108 | —C₂H₅ | —C₂H₅ | —CH₂CH₂OCH₃ | —CH(CH₃)—CH=CH₂ | O | M.P. 67–69° C. |
| 109 | —C₂H₅ | —C₂H₅ | —CHF₂ | —CH(CH₃)₂ | O | M.P. 89–90° C. |
| 110 | —Cl | —OCH₃ | —C₂H₅ | —CH(CH₃)₂ | O | M.P. 121–122° C. |
| 111 | —Cl | —OCH₃ | —CH₂C≡CH | —CH₃ | O | $n_D^{22}$ 1.5619 |
| 112 | —Cl | —OCH₃ | —CH₂C≡CH | —CH(CH₃)₂ | O | M.P. 72–73° C. |
| 113 | —Br | —OCH₃ | —C₂H₅ | —CH(CH₃)₂ | O | M.P. 144.5–145° C. |
| 114 | —Br | —OCH₃ | —C₂H₅ | —CH₂C≡CCH₂Cl | O | $n_D^{19.7}$ 1.5685 |
| 115 | —Cl | —OC₂H₅ | —C₂H₅ | —CH₃ | O | M.P. 98.5–99.5° C. |
| 116 | —Cl | —OC₂H₅ | —C₂H₅ | —C₂H₅ | O | M.P. 110–111° C. |
| 117 | —Cl | —OC₂H₅ | —C₂H₅ | —CH(CH₃)₂ | O | M.P. 113–115° C. |
| 118 | —Cl | —OC₂H₅ | —C₂H₅ | —CH(CH₃)(C₂H₅) | O | M.P. 94–95° C. |
| 119 | —Cl | —OC₂H₅ | —C₂H₅ | —CH₂CH=CH₂ | O | M.P. 89–90° C. |
| 120 | —Cl | —OC₂H₅ | —C₂H₅ | —CH₂C≡CH | O | M.P. 98.5–99.5° C. |
| 121 | —Cl | —OC₂H₅ | —C₂H₅ | —CH(CH₃)—C₄H₉(n) | O | $n_D^{18.0}$ 1.5172 |
| 122 | —Cl | —OC₂H₅ | —C₂H₅ | —CH(CH₃)—C₆H₁₃(n) | O | $n_D^{19.5}$ 1.5121 |

TABLE 1-continued

Structure:
$R^1O$-phenyl with X (ortho to OR¹), Y (other ortho to OR¹), and $NHCZR^2$ (para to OR¹), where the amide is $-NH-C(=O)-Z-R^2$

| Compound No. | X | Y | R¹ | R² | Z | Physical constant |
|---|---|---|---|---|---|---|
| 123 | —Cl | —OC$_2$H$_5$ | —C$_2$H$_5$ | —CH(CH$_3$)—CH=CH$_2$ | O | M.P. 90–91° C. |
| 124 | —Cl | —OC$_2$H$_5$ | —C$_2$H$_5$ | —CH(CH$_3$)—C≡CH | O | M.P. 120.5–122° C. |
| 125 | —Cl | —OC$_2$H$_5$ | —C$_2$H$_5$ | —CH(C$_5$H$_{11}$(n))—CH=CH$_2$ | O | $n_D^{17.0}$ 1.5191 |
| 126 | —Cl | —OC$_2$H$_5$ | —C$_2$H$_5$ | —CH(C$_5$H$_{11}$(n))—C≡CH | O | $n_D^{16.5}$ 1.5186 |
| 127 | —Cl | —OC$_2$H$_5$ | —C$_2$H$_5$ | —CH(C$_2$H$_5$)—CH$_2$Br | O | M.P. 61–62° C. |
| 128 | —Cl | —OC$_2$H$_5$ | —C$_2$H$_5$ | —CH$_2$C≡CCH$_2$Cl | O | $n_D^{20.5}$ 1.5466 |
| 129 | —Cl | —OC$_2$H$_5$ | —C$_2$H$_5$ | —CH(CH$_3$)—CH$_2$OCH$_3$ | O | $n_D^{18.0}$ 1.5206 |
| 130 | —Cl | —OC$_2$H$_5$ | —C$_2$H$_5$ | —CH(CH$_3$)—CH$_2$O—C$_4$H$_9$(n) | O | $n_D^{17}$ 1.5140 |
| 131 | —Cl | —OC$_2$H$_5$ | —C$_2$H$_5$ | —CH$_2$CH$_2$C≡N | O | M.P. 100.5–101.5° C. |
| 132 | —Cl | —OC$_2$H$_5$ | —CH$_2$CH=CH$_2$ | —CH(CH$_3$)$_2$ | O | M.P. 56–57° C. |
| 133 | —Cl | —OC$_2$H$_5$ | —CH$_2$CH=CH$_2$ | —CH(CH$_3$)—CH$_2$OCH$_3$ | O | $n_D^{18.5}$ 1.5331 |
| 134 | —Cl | —OC$_2$H$_5$ | —CH$_2$C≡CH | —CH(CH$_3$)$_2$ | O | $n_D^{19.5}$ 1.5202 |
| 135 | —Cl | —OC$_2$H$_5$ | —CH$_2$CH=CHCH$_3$ | —CH(CH$_3$)$_2$ | O | $n_D^{22.0}$ 1.5198 |
| 136 | —Cl | —OC$_2$H$_5$ | —CH$_2$CH$_2$Cl | —CH(CH$_3$)$_2$ | O | $n_D^{20.0}$ 1.5323 |
| 137 | —Br | —OC$_2$H$_5$ | —C$_2$H$_5$ | —CH(CH$_3$)$_2$ | O | M.P. 115.5–116.5° C. |

TABLE 1-continued structure: R¹O-phenyl with X (top), Y (bottom), NHC(=O)ZR² substituent

| Compound No. | X | Y | R¹ | R² | Z | Physical constant |
|---|---|---|---|---|---|---|
| 138 | —CH₃ | —OCH₃ | —C₂H₅ | —CH(CH₃)₂ | O | M.P. 116.5–118° C. |
| 139 | —CH₃ | —OC₂H₅ | —C₂H₅ | —CH₃ | O | $n_D^{20.5}$ 1.5212 |
| 140 | —CH₃ | —OC₂H₅ | —C₂H₅ | —C₂H₅ | O | M.P. 69–70° C. |
| 141 | —CH₃ | —OC₂H₅ | —C₂H₅ | —CH(CH₃)₂ | O | M.P. 86–87.5° C. |
| 142 | —CH₃ | —OC₂H₅ | —C₂H₅ | —CH(CH₃)(C₂H₅) | O | M.P. 76–77° C. |
| 143 | —CH₃ | —OC₂H₅ | —C₂H₅ | —CH₂C≡CH | O | M.P. 85.5–86.5° C. |
| 144 | —CH₃ | —OC₂H₅ | —C₂H₅ | —CH(CH₃)—CH=CH₂ | O | M.P. 74–75° C. |
| 145 | —CH₃ | —OC₂H₅ | —C₂H₅ | —CH(CH₃)—C≡CH | O | M.P. 121–122.5° C. |
| 146 | —CH₃ | —OC₂H₅ | —C₂H₅ | —CH(CH₃)—CH₂OCH₃ | O | M.P. 57–59° C. |
| 147 | —CH₃ | —OC₂H₅ | —C₂H₅ | —CH₂CH₂OCH₂—C₆H₅ | O | $n_D^{17.5}$ 1.5425 |
| 148 | —CH₃ | —OC₂H₅ | —C₂H₅ | —CH₂CH₂OCH₂CH₂Cl | O | M.P. 98–99.5° C. |
| 149 | —CH₃ | —OC₂H₅ | —C₂H₅ | —CH(CH₃)—cyclopentyl | O | M.P. 63–64.5° C. |
| 150 | —CH₃ | —OC₂H₅ | —C₂H₅ | —CH(CH₃)—CH₂O—C₆H₅ | O | M.P. 135.5–137° C. |
| 151 | —CH₃ | —OC₂H₅ | —C₂H₅ | —CH₂C≡CCH₂Cl | O | $n_D^{19.5}$ 1.5361 |
| 152 | —CH₃ | —OC₂H₅ | —CH₂C≡CH | —CH(CH₃)₂ | O | $n_D^{17.5}$ 1.5112 |
| 153 | —C₂H₅ | —OCH₃ | —CH₃ | —CH(CH₃)₂ | O | M.P. 80.5–81° C. |
| 154 | —C₂H₅ | —OCH₃ | —CH₃ | —CH₂C≡CCH₃ | O | $n_D^{23.2}$ 1.5375 |

TABLE 1-continued $$R^1O-\underset{Y}{\underset{|}{\overset{X}{\underset{|}{C_6H_3}}}}-NHCZR^2$$
(with C(=O) as the NHCZR² linker, Z shown separately)

| Compound No. | X | Y | R¹ | R² | Z | Physical constant |
|---|---|---|---|---|---|---|
| 155 | —C₂H₅ | —OCH₃ | —CH₃ | —CH(CH₃)(CH₂OCH₃) | O | $n_D^{25.5}$ 1.5092 |
| 156 | —CH=CH₂ | —OCH₃ | —CH₃ | —CH(CH₃)₂ | O | M.P. 105.5–107° C. |
| 157 | —C₂H₅ | —OC₂H₅ | —C₂H₅ | —CH(CH₃)₂ | O | M.P. 100–101° C. |
| 158 | —CH₂CH₂CH₃ | —OC₂H₅ | —C₂H₅ | —CH(CH₃)₂ | O | M.P. 114–115° C. |
| 159 | —CH=CHCH₃ | —OC₂H₅ | —C₂H₅ | —CH(CH₃)₂ | O | M.P. 89–98° C. |
| 160 | —CH=CH₂ | —OC₂H₅ | —C₂H₅ | —CH(CH₃)₂ | O | M.P. 127.5–128.5° C. |
| 161 | —CH₂CH₂CH₂CH₃ | —OC₂H₅ | —C₂H₅ | —CH(CH₃)₂ | O | M.P. 76–77° C. |
| 162 | —OCH₃ | —OCH₃ | —CH₃ | —CH(CH₃)₂ | O | M.P. 121.5–122.5° C. |
| 163 | —OCH₃ | —OCH₃ | —C₂H₅ | —CH(CH₃)₂ | O | M.P. 163–164.5° C. |
| 164 | —OCH₃ | —OCH₃ | —C₂H₅ | —CH₂CH=CHCH₃ | O | M.P. 112.5–113.5° C. |
| 165 | —OCH₃ | —OCH₃ | —C₂H₅ | —CH(CH₃)-cyclopropyl | O | M.P. 138° C. (decomp.) |
| 166 | —OCH₃ | —OC₂H₅ | —C₂H₅ | —CH(CH₃)₂ | O | M.P. 124–125° C. |
| 167 | —OC₂H₅ | —OC₂H₅ | —C₂H₅ | —CH(CH₃)₂ | O | M.P. 147–149° C. |

TABLE 1-continued $$R^1O-\underset{Y}{\overset{X}{\underset{|}{\bigcirc}}}-NHCZR^2$$ (with C=O shown as $\overset{O}{\underset{\|}{C}}$)

| Compound No. | X | Y | R¹ | R² | Z | Physical constant |
|---|---|---|---|---|---|---|
| 168 | —CH₂OCH₃ | —OC₂H₅ | —C₂H₅ | —CH(CH₃)₂ | O | M.P. 107–108° C. |
| 169 | —CH₂OCH₃ | —OC₂H₅ | —C₂H₅ | —CH(CH₃)—CH₂OCH₃ | O | M.P. 61–66° C. |
| 170 | —CH₂OC₂H₅ | —OC₂H₅ | —C₂H₅ | —CH₂C≡CCH₃ | O | M.P. 79.5–80.5° C. |
| 171 | —CH₂OCH₂CH=CH₂ | —OC₂H₅ | —C₂H₅ | —CH(CH₃)—C≡CH | O | M.P. 68.5–69° C. |
| 172 | —CH₂OCH₂C≡CH | —OC₂H₅ | —C₂H₅ | —CH₂CH=CHCH₃ | O | $n_D^{24.0}$ 1.5279 |
| 173 | —CH₂OCH₂CH₂F | —OC₂H₅ | —C₂H₅ | —CH₂C≡CCH₂Cl | O | $n_D^{22.5}$ 1.5277 |
| 174 | —CH₂OCH₃ | —Cl | —C₂H₅ | —CH(CH₃)₂ | O | $n_D^{19.7}$ 1.5221 |
| 175 | —C(=O)—OCH₃ | —OC₂H₅ | —C₂H₅ | —CH(CH₃)₂ | O | M.P. 116–118° C. |
| 176 | —C(=O)—OC₂H₅ | —OC₂H₅ | —C₂H₅ | —CH₂CH=CHCH₂Cl | O | M.P. 64–65° C. |
| 177 | —C(=O)—OCH₂CH=CH₂ | —OC₂H₅ | —C₂H₅ | —CH(CH₃)₂ | O | M.P. 110–111° C. |
| 178 | —C(=O)—OCH₂CH₂F | —OC₂H₅ | —C₂H₅ | —CH(CH₃)₂ | O | M.P. 118–119° C. |
| 179 | —C(=O)—OCH₂C≡CH | —OC₂H₅ | —C₂H₅ | —CH(CH₃)₂ | O | M.P. 124–125° C. |
| 180 | —CH₂OCH₃ | —CH₃ | —C₂H₅ | —C₂H₅ | O | $n_D^{17}$ 1.5198 |
| 181 | —C≡N | —OC₂H₅ | —C₂H₅ | —CH(CH₃)₂ | O | M.P. 108.5–109.5° C. |
| 182 | —C≡N | —CH₃ | —C₂H₅ | —CH(CH₃)₂ | O | $n_D^{20}$ 1.5265 |

TABLE 1-continued

| Compound No. | X | Y | R¹ | R² | Z | Physical constant |
|---|---|---|---|---|---|---|
| 183 | $-CH_2C\equiv N$ | $-OC_2H_5$ | $-C_2H_5$ | $-CH(CH_3)_2$ | O | M.P. 101–103° C. |
| 184 | $-CH_2CH_2C\equiv N$ | $-OC_2H_5$ | $-C_2H_5$ | $-CH(CH_3)_2$ | O | $n_D^{16.7}$ 1.5089 |
| 185 | $-CH=CHC\equiv N$ | $-OC_2H_5$ | $-C_2H_5$ | $-CH(CH_3)_2$ | O | M.P. 97–100° C. |
| 186 | $-\underset{\underset{O}{\|}}{C}-H$ | $-OC_2H_5$ | $-C_2H_5$ | $-CH(CH_3)_2$ | O | M.P. 103.5–105° C. |
| 187 | $-CH(OCH_3)_2$ | $-OC_2H_5$ | $-C_2H_5$ | $-CH(CH_3)_2$ | O | $n_D^{17.2}$ 1.5145 |
| 188 | $-CH(OC_2H_5)_2$ | $-OC_2H_5$ | $-C_2H_5$ | $-CH(CH_3)_2$ | O | $n_D^{17.2}$ 1.5072 |
| 189 | $-CH\begin{smallmatrix}O-CH_2\\O-CH_2\end{smallmatrix}$ | $-OC_2H_5$ | $-C_2H_5$ | $-CH(CH_3)_2$ | O | M.P. 97–99° C. |
| 190 | $-CH=NOH$ | $-OC_2H_5$ | $-C_2H_5$ | $-CH(CH_3)_2$ | O | M.P. 172–173.5° C. |
| 191 | $-CH=NOCH_3$ | $-OC_2H_5$ | $-C_2H_5$ | $-CH(CH_3)_2$ | O | M.P. 110–111.5° C. |
| 192 | $-C\equiv CH$ | $-OC_2H_5$ | $-C_2H_5$ | $-CH(CH_3)_2$ | O | M.P. 154.5–156° C. |
| 193 | $-CH(Br)-CH_2Br$ | $-OC_2H_5$ | $-C_2H_5$ | $-CH(CH_3)_2$ | O | M.P. 111–121° C. |
| 194 | $-\underset{\underset{O}{\|}}{C}-NH_2$ | $-OC_2H_5$ | $-C_2H_5$ | $-CH(CH_3)_2$ | O | M.P. 187–192° C. |

TABLE 1-continued $$R^1O-\text{C}_6H_3(X)(Y)-NHC(=O)ZR^2$$

| Compound No. | X | Y | $R^1$ | $R^2$ | Z | Physical constant |
|---|---|---|---|---|---|---|
| 195 | −C(=O)NHCH₃ | −OC₂H₅ | −C₂H₅ | −CH(CH₃)₂ | O | M.P. 141–143° C. |
| 196 | −C(=O)CH₃ | −OC₂H₅ | −C₂H₅ | −CH(CH₃)₂ | O | M.P. 88–90° C. |
| 197 | −CH₂OH | −OC₂H₅ | −C₂H₅ | −CH(CH₃)₂ | O | M.P. 117–118° C. |
| 198 | −CH₂OH | −OC₂H₅ | −C₂H₅ | −CH(CH₃)(C₂H₅) | O | M.P. 86–87.5° C. |
| 199 | −CH₃ | −CH₃ | −C₂H₅ | −C₂H₅ | S | $n_D^{20}$ 1.5623 |
| 200 | −CH₃ | −CH₃ | −C₂H₅ | −CH(CH₃)₂ | S | M.P. 73.5–75° C. |
| 201 | −OC₂H₅ | −Cl | −C₂H₅ | −CH(CH₃)₂ | S | M.P. 70–71.5° C. |
| 202 | −OC₂H₅ | −Cl | −C₂H₅ | −CH(CH₃)(C₂H₅) | S | M.P. 80.5–81.5° C. |
| 203 | −OC₂H₅ | −CH₃ | −C₂H₅ | −C₂H₅ | S | M.P. 84.5–85.5° C. |
| 204 | −OC₂H₅ | −CH₃ | −C₂H₅ | −CH(CH₃)₂ | S | M.P. 71–72° C. |
| 205 | −OC₂H₅ | −CH₃ | −C₂H₅ | −CH(CH₃)(C₂H₅) | S | M.P. 84.5–85.5° C. |
| 206 | −CH₃ | −CH₃ | −CH₃ | −CH(CH₃)−C≡CH | O | M.P. 67.5–68.5° C. |
| 207 | −CH₃ | −CH₃ | −CH₃ | −CH(CH₂CH₃)−C≡CH | O | $n_D^{25}$ 1.5269 |
| 208 | −CH₂OCH₃ | −CH₃ | −C₂H₅ | −CH(CH₃)₂ | O | $n_D^{18.5}$ 1.5132 M.P. 68–69° C. |

TABLE 1-continued

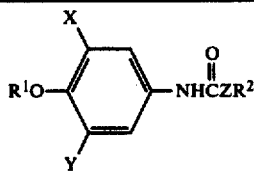

| Compound No. | X | Y | R¹ | R² | Z | Physical constant |
|---|---|---|---|---|---|---|
| 209 | —CH$_2$OCH$_3$ | —CH$_3$ | —C$_2$H$_5$ | —CH$_3$ | O | $n_D^{17}$ 1.5219 |

In the practical use of the N-phenylcarbamates (I) as a fungicide, they may be applied as such or in any preparation form such as dusts, wettable powders, oil sprays, emulsifiable concentrates, tablets, granules, fine granules, aerosols or flowables. Such preparation forms can be prepared in a conventional manner by mixing at least one of the N-phenylcarbamates (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are botanical materials (e.g. flour, tobacco stalk powder, soybean powder, walnut-shell powder, vegetable powder, saw dust, bran, bark powder, cellulose powder, vegetable extract residue), fibrous materials (e.g. paper, corrugated card-board, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the liquid carriers or diluents are water, alcohols (e.g., methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include cesein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixtures), TCP (tricresyl phosphate), tolu oil, epoxydized oil, various surfactants, verious fatty acids and their esters, etc.

The foregoing preparations generally contain at least one of the N-phenylcarbamates (I) in a concentration of about 1 to 95% by weight, preferably 2.0 to 80% by weight. By using the preparations, the N-phenylcarbamates (I) are generally applied in such amounts as 2 to 100 g per 10 are.

When only the drug-resistant strains of phytopathogenic fungi are present, the N-phenylcarbamates (I) may be used alone. However, when the drug-sensitive strains are present together with the drug-resistant strains, their alternate use with benzimidazole thiophanate fungicides and/or cyclic imide fungicides or their combined use with benzimidazole thiophanate fungicides and/or cyclic imide fungicides is favorable. In such alternate or combined use, each active ingredient may be employed as such or in conventional agricultural preparation forms. In case of the combined use, the weight proportion of the N-phenylcarbamate (I) and the benzimidazole thiophanate fungicide and/or the cyclic imide fungicide may be from about 1:0.1 to 1:10.0.

Typical examples of the benzimidazole thiophanate fungicides and the cyclic imide fungicides are shown in Table 2.

TABLE 2

| Compound No. | Structure | Name |
|---|---|---|
| A | benzimidazole with NHCOOCH$_3$ at 2-position and CONHC$_4$H$_9$(n) on N | Methyl 1-(butyl-carbamoyl)benz-imidazol-2-yl-carbamate |
| B | 2-(4-thiazolyl)benzimidazole structure | 2-(4-Thiazolyl)benz-imidazole |
| C | benzimidazole with NHCOOCH$_3$ | Methyl benzimidazol-2-ylcarbamate |

TABLE 2-continued

| Compound No. | Structure | Name |
|---|---|---|
| D | 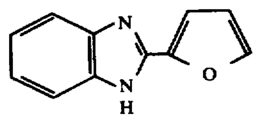 | 2-(2-Furyl)benzimidazole |
| E | 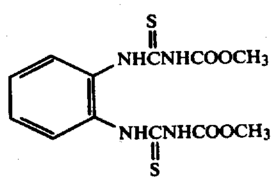 | 1,2-Bis(3-methoxycarbonyl-2-thioureido)benzene |
| F | 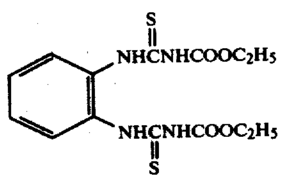 | 1,2-Bis(3-ethoxycarbonyl-2-thioureido)benzene |
| G | 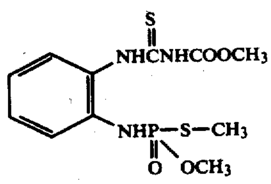 | 2-(O,S—Dimethylphosphorylamino)-1-(3'-methoxycarbonyl-2'-thioureido)benzene |
| H | 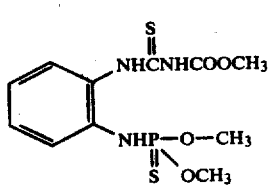 | 2-(O,O—Dimethylthiophosphorylamino)-1-(3'-methoxycarbonyl-2'-thioureido)benzene |
| I | 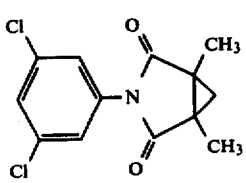 | N—(3',5'-Dichlorophenyl)-1,2-dimethylcyclopropane-1,2-dicarboximide |
| J | 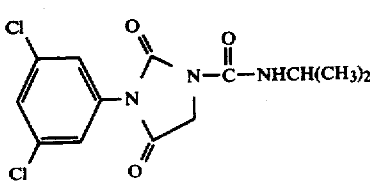 | 3-(3',5'-Dichlorophenyl)-1-isopropyl carbamoylimidazolidin-2,4-dione |
| K | 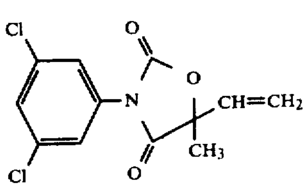 | 3-(3',5'-Dichlorophenyl)-5-methyl-5-vinyloxazolidin-2,4-dione |

TABLE 2-continued

| Compound No. | Structure | Name |
|---|---|---|
| L | (dichlorophenyl oxazolidine structure with COOC$_2$H$_5$ and CH$_3$ groups) | Ethyl (RS)-3-(3',5'-dichlorophenyl)-5-methyl-2,4-dioxo-oxazolidine-5-carboxylate |

In addition, the N-phenylcarbamates (I) may be used in admixture with other fungicides (except benzimidazole thiophanate fungicides and cyclic imide fungicides), herbicides, insecticides, miticides, fertilizers, etc.

When the N-phenylcarbamates (I) are used as fungicides, they may be applied in such amounts as to 2 to 100 grams per 10 ares. However, this amount may vary depending upon preparation forms, application times, application methods, application sites, diseases, crops and so on, and therefore, they are not limited to said particular amounts.

Some practical embodiments of the fungicidal composition according to the invention are illustratively shown in the following Examples wherein % and part(s) are by weight.

PREPARATION EXAMPLE 1

Two parts of Compound No. 2, 88 parts of clay and 10 parts of talc were thoroughly pulverized and mixed together to obtain a dust preparation containing 2% of the active ingredient.

PREPARATION EXAMPLE 2

Thirty parts of Compound No. 15, 45 parts of diatomaceous earth, 20 parts of white carbon, 3 parts of sodium laurylsulfate as a wetting agent and 2 parts of calcium ligninsulfonate as a dispersing agent were mixed while being powdered to obtain a wettable powder preparation containing 30% of the active ingredient.

PREPARATION EXAMPLE 3

Fifty parts of Compound No. 5, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredient.

PREPARATION EXAMPLE 4

Ten parts of Compound No. 22, 80 parts of cyclohexanone and 10 parts of polyoxyethylene alkylaryl ether as an emulsifier were mixed together to obtain an emulsifiable concentrtate preparation containing 10% of the active ingredient.

PREPARATION EXAMPLE 5

Two parts of Compound No. 107, 88 parts of clay and 10 parts of talc were thoroughly pulverized and mixed together to obtain a dust preparation containing 2% of the active ingredient.

PREPARATION EXAMPLE 6

Thirty parts of Compound No. 54, 45 parts of diatomaceous earth, 20 parts of white carbon, 3 parts of sodium laurylsulfate as a wetting agent and 2 parts of calcium ligninsulfonate as a dispersing agent were mixed while being powdered to obtain a wettable powder preparation containing 30% of the active ingredient.

PREPARATION EXAMPLE 7

Fifty parts of Compound No. 164, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredient.

PREPARATION EXAMPLE 8

Ten parts of Compound No. 101, 80 parts of cyclohexanone and 10 parts of polyoxyethylene alkylaryl ether as an emulsifier were mixed together to obtain an emulsifiable concentrate preparation containing 10% of the active ingredient.

PREPARATION EXAMPLE 9

Two parts of Compound No. 44, 88 parts of clay and 10 parts of talc were thoroughly pulverized and mixed together to obtain a dust preparation containing 2% of the active ingredient.

PREPARATION EXAMPLE 10

Thirty parts of Compound No. 79, 45 parts of diatomaceous earth, 20 parts of white carbon, 3 parts of sodium laurylsulfate as a wetting agent and 2 parts of calcium ligninsulfonate as a dispersing agent were mixed while being powdered to obtain a wettable powder preparation containing 30% of the active ingredient.

PREPARATION EXAMPLE 11

Fifty parts of Compound No. 29, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredient.

PREPARATION EXAMPLE 12

Ten parts of Compound No. 81, 80 parts of cyclohexanone and 10 parts of polyoxyethylene alkylaryl ether as an emulsifier were mixed together to obtain an emulsifiable concentrate preparation containing 10% of the active ingredient.

PREPARATION EXAMPLE 13

One part of Compound No. 15, 1 part of Compound No. I, 88 parts of clay and 10 parts of talc were thoroughly pulverized and mixed together to obtain a dust preparation containing 2% of the active ingredients.

PREPARATION EXAMPLE 14

Two parts of Compound No. 105, 2 parts of Compound No. E, 86 parts of clay and 10 parts of talc were thoroughly pulverized and mixed together to obtain a dust preparation containing 4% of the active ingredients.

PREPARATION EXAMPLE 15

Twenty parts of Compound No. 141, 10 parts of Compound No. J, 45 parts of diatomaceous earth, 20 parts of white carbon, 3 parts of sodium laurylsulfate as a wetting agent and 2 parts of calcium ligninsulfonate as a dispersing agent were mixed while being powdered to obtain a wettable powder preparation containing 30% of the active ingredients.

PREPARATION EXAMPLE 16

Ten parts of Compound No. 181, 40 parts of Compound No. B, 45 parts of diatomaceous earth, 2.5 parts of calcium alkylbenzenesulfonate as a wetting agent and 2.5 parts of calcium ligninsulfonate as a dispersing agent were mixed while being powdered to obtain a wettable powder preparation containing 50% of the active ingredients.

PREPARATION EXAMPLE 17

Twenty-five parts of Compound No. 54, 50 parts of Compound No. I, 18 parts of diatomaceous earth, 3.5 parts of calcium alkylbenzenesulfonate as a wetting agent and 3.5 parts of calcium ligninsulfonate as a dispersing agent were mixed while being powdered to obtain a wettable powder preparation containing 75% of the active ingredients.

PREPARATION EXAMPLE 18

Twenty parts of Compound No. 105, 30 parts of Compound No. A, 40 parts of powdery sucrose, 5 parts of white carbon, 3 parts of sodium laurylsulfate as a wetting agent and 2 parts of calcium ligninsulfonate as a dispersing agent were mixed while being powdered to obtain a wettable powder preparation containing 50% of the active ingredients.

Typical test data indicating the excellent fungicidal activity of the N-phenylcarbamates (I) are shown below. The compounds used for comparison are as follows:

| Compound | Remarks |
|---|---|
| Control (a) — 3-Cl-C$_6$H$_4$-NHCOCH$_3$ | Synthesized for comparison |
| Control (b) — 4-Cl-C$_6$H$_4$-NHCOCH$_3$ | Synthesized for comparison |
| Control (c) — 2-Cl-C$_6$H$_4$-NHCOCH$_3$ | Synthesized for comparison |
| Control (d) — 3-Cl-C$_6$H$_4$-NHCOC$_2$H$_5$ | Synthesized for comparison |
| Control (e) — 4-Cl-C$_6$H$_4$-NHCOC$_2$H$_5$ | Synthesized for comparison |
| Control (f) — 2-Cl-C$_6$H$_4$-NHCOC$_2$H$_5$ | Synthesized for comparison |
| Control (g) — 3-Br-C$_6$H$_4$-NHCOCH$_3$ | Synthesized for comparison |
| Control (h) — 3-Br-C$_6$H$_4$-NHCOC$_2$H$_5$ | Synthesized for comparison |
| Control (i) — 3,4-Cl$_2$-C$_6$H$_3$-NHCOCH(CH$_3$)$_2$ | Agricultural Biological Chemistry, 35, 1707–1719 (1971) |
| Control (j) — 3,4-Cl$_2$-C$_6$H$_3$-NHCOCH$_2$CH=CH$_2$ | Agricultural Biological Chemistry, 35, 1707–1719 (1971) |
| Control (k) — 3,4-Cl$_2$-C$_6$H$_3$-NHCOCH$_2$CH$_2$Cl | Agricultural Biological Chemistry, 35, 1707–1719 (1971) |

| Compound | Remarks |
|---|---|
| Control (I) 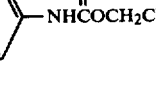 | Agricultural Biological Chemistry, 35, 1707–1719 (1971) |
| Swep 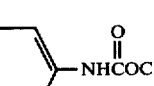 | Commercially available herbicide |
| Chlorpropham 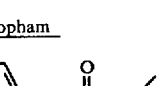 | Commercially available herbicide |
| Barban  | Commercially available herbicide |
| CEPC  | Commercially available herbicide |
| Propham 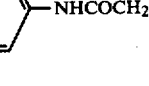 | Commercially available herbicide |
| Chlorbufam 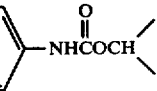 | Commercially available herbicide |
| Benomyl 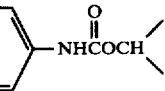 | Commercially available fungicide |
| Thiophanate-methyl 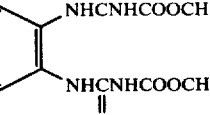 | Commercially available fungicide |
| Carbendazim 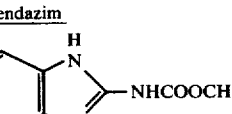 | Commercially available fungicide |
| Thiabendazole 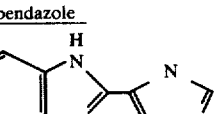 | Commercially available fungicide |
| Edifenphos 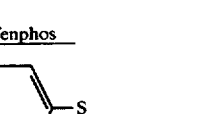 | Commercially available fungicide |

Experiment 1

Protective activity test on powdery mildew of cucumber (*Sphaerotheca fuliginea*):

A flower pot of 90 ml volume was filed with sandy soil, and seeds of cucumber (var: Sagami-hanjiro) were sown therein. Cultivation was carried out in a greenhouse for 8 days. Onto the resulting seedlings having cotyledons, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Sphaerotheca fuliginea* by spraying and further cultivated in the greenhouse. Ten days thereafter, the infectious state of the plants was observed. The degree of damage was determined in the following manner, and the results are shown in Table 3.

The leaves examined were measured for a percentage of infected area and classified into the corresponding disease indices, 0, 0.5, 1, 2, 4:

| Disease index | Percentage of infected area |
|---|---|
| 0 | No infection |
| 0.5 | Infected area of less than 5% |
| 1 | Infected area of less than 20% |
| 2 | Infected area of less than 50% |
| 4 | Infected area of not less than 50% |

The disease severity was calculated according to the following equation:

$$\text{Disease severity (\%)} = \frac{\Sigma \text{ (Disease index)} \times \text{(Number of leaves)}}{4 \times \text{(Total number of leaves examined)}} \times 100$$

The prevention value was calculated according to the following equation:

$$\text{Prevention value (\%)} = 100 - \frac{\text{(Disease severity in treated plot)}}{\text{(Disease severity in untreated plot)}} \times 100$$

TABLE 3

| Compound No. | Concentration of active ingredient (ppm) | Prevention value when inoculated with drug-resistant strain (%) | Prevention value when inoculated with drug-sensitive strain (%) |
|---|---|---|---|
| 2 | 200 | 100 | 0 |
| 6 | 200 | 100 | 0 |
| 7 | 200 | 100 | 0 |
| 13 | 200 | 97 | 0 |
| 15 | 200 | 100 | 0 |
| 19 | 200 | 100 | 0 |
| 20 | 200 | 100 | 0 |
| 22 | 200 | 100 | 0 |
| 24 | 200 | 100 | 0 |
| 28 | 200 | 97 | 0 |
| 29 | 200 | 100 | 0 |
| 31 | 200 | 94 | 0 |
| 32 | 200 | 97 | 0 |
| 33 | 200 | 100 | 0 |
| 36 | 200 | 97 | 0 |
| 39 | 200 | 94 | 0 |
| 44 | 200 | 97 | 0 |
| 50 | 200 | 97 | 0 |
| 51 | 200 | 100 | 0 |
| 52 | 200 | 97 | 0 |
| 54 | 200 | 100 | 0 |
| 55 | 200 | 100 | 0 |
| 57 | 200 | 100 | 0 |
| 58 | 200 | 100 | 0 |
| 59 | 200 | 100 | 0 |
| 60 | 200 | 100 | 0 |
| 61 | 200 | 100 | 0 |
| 62 | 200 | 100 | 0 |
| 63 | 200 | 100 | 0 |
| 64 | 200 | 100 | 0 |
| 65 | 200 | 100 | 0 |
| 68 | 200 | 100 | 0 |
| 70 | 200 | 100 | 0 |
| 71 | 200 | 100 | 0 |
| 73 | 200 | 100 | 0 |
| 74 | 200 | 100 | 0 |
| 77 | 200 | 100 | 0 |
| 78 | 200 | 100 | 0 |
| 79 | 200 | 100 | 0 |
| 80 | 200 | 100 | 0 |
| 84 | 200 | 100 | 0 |
| 86 | 200 | 100 | 0 |
| 88 | 200 | 94 | 0 |
| 90 | 200 | 100 | 0 |
| 91 | 200 | 100 | 0 |
| 92 | 200 | 97 | 0 |
| 99 | 200 | 100 | 0 |
| 101 | 200 | 100 | 0 |
| 102 | 200 | 100 | 0 |
| 103 | 200 | 100 | 0 |
| 105 | 200 | 100 | 0 |
| 109 | 200 | 100 | 0 |
| 110 | 200 | 100 | 0 |
| 111 | 200 | 100 | 0 |
| 112 | 200 | 100 | 0 |
| 115 | 200 | 100 | 0 |
| 116 | 200 | 100 | 0 |
| 117 | 200 | 100 | 0 |
| 118 | 200 | 100 | 0 |
| 119 | 200 | 100 | 0 |
| 120 | 200 | 100 | 0 |
| 122 | 200 | 100 | 0 |
| 124 | 200 | 100 | 0 |
| 127 | 200 | 100 | 0 |
| 129 | 200 | 100 | 0 |
| 130 | 200 | 100 | 0 |
| 131 | 200 | 100 | 0 |
| 132 | 200 | 100 | 0 |
| 133 | 200 | 100 | 0 |
| 134 | 200 | 100 | 0 |
| 135 | 200 | 100 | 0 |
| 138 | 200 | 100 | 0 |
| 140 | 200 | 100 | 0 |
| 141 | 200 | 100 | 0 |
| 142 | 200 | 100 | 0 |
| 143 | 200 | 100 | 0 |
| 146 | 200 | 100 | 0 |
| 147 | 200 | 100 | 0 |
| 152 | 200 | 100 | 0 |
| 157 | 200 | 100 | 0 |
| 159 | 200 | 100 | 0 |
| 165 | 200 | 100 | 0 |
| 167 | 200 | 100 | 0 |
| 174 | 200 | 100 | 0 |
| 181 | 200 | 100 | 0 |
| 193 | 200 | 100 | 0 |
| Control (a) | 200 | 0 | 0 |
| Control (b) | 200 | 0 | 0 |
| Control (c) | 200 | 0 | 0 |
| Control (d) | 200 | 0 | 0 |
| Control (e) | 200 | 0 | 0 |
| Control (f) | 200 | 0 | 0 |
| Control (g) | 200 | 0 | 0 |
| Control (h) | 200 | 0 | 0 |
| Control (i) | 200 | 0 | 0 |
| Control (j) | 200 | 0 | 0 |
| Control (k) | 200 | 0 | 0 |
| Control (l) | 200 | 0 | 0 |
| Swep | 200 | 0 | 0 |
| Chlorpropham | 200 | 0 | 0 |
| Barban | 200 | 25 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 3, the N-phenylcarbamates (I) of the invention show an excellent preventive effect on the drug-resistant strain but do not show any preventive effect on the tested drug-sensitive strain. To the contrary, commercially available known fungicides such as Benomyl, Thiophanate-methyl and Carbendazim show a notable controlling effect on the drug-sensitive strain but not on the drug-resistant strain. Other tested compounds structurally similar to the N-phenylcarbamates (I) do not show any fungicidal activity on the drug-sensitive strain and the drug-resistant strain.

Experiment 2

Preventive effect on cercospora leaf spot of sugarbeet (*Cercospora beticola*):

A flower pot of 90 ml volume was filled with sandy soil, and seeds of sugarbeet (var: Detroit dark red) were sown therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora beticola* by spraying. The pot was covered with a polyvinyl chloride sheet to make a condition of high humidity, and cultivation was continued in the greenhouse for 10 days. The degree of damage was determined in the same manner as in Experiment 1, and the results are shown in Table 4.

TABLE 4

| Compound No. | Concentration of active ingredient (ppm) | Prevention value when inoculated with drug-resistant strain (%) | Prevention value when inoculated with drug-sensitive strain (%) |
|---|---|---|---|
| 2 | 200 | 100 | 0 |
| 6 | 200 | 96 | 0 |
| 7 | 200 | 100 | 0 |
| 8 | 200 | 100 | 0 |
| 13 | 200 | 97 | 0 |
| 15 | 200 | 100 | 0 |
| 19 | 200 | 100 | 0 |
| 20 | 200 | 100 | 0 |
| 22 | 200 | 100 | 0 |
| 24 | 200 | 100 | 0 |
| 28 | 200 | 99 | 0 |
| 29 | 200 | 100 | 0 |
| 31 | 200 | 94 | 0 |
| 32 | 200 | 100 | 0 |
| 33 | 200 | 100 | 0 |
| 36 | 200 | 97 | 0 |
| 38 | 200 | 94 | 0 |
| 40 | 200 | 100 | 0 |
| 41 | 200 | 100 | 0 |
| 44 | 200 | 96 | 0 |
| 47 | 200 | 94 | 0 |
| 50 | 200 | 100 | 0 |
| 51 | 200 | 100 | 0 |
| 52 | 200 | 100 | 0 |
| 54 | 200 | 100 | 0 |
| 55 | 200 | 100 | 0 |
| 57 | 200 | 100 | 0 |
| 58 | 200 | 100 | 0 |
| 59 | 200 | 100 | 0 |
| 60 | 200 | 100 | 0 |
| 64 | 200 | 100 | 0 |
| 68 | 200 | 100 | 0 |
| 74 | 200 | 100 | 0 |
| 78 | 200 | 100 | 0 |
| 79 | 200 | 100 | 0 |
| 80 | 200 | 100 | 0 |
| 81 | 200 | 96 | 0 |
| 86 | 200 | 100 | 0 |
| 88 | 200 | 100 | 0 |
| 90 | 200 | 100 | 0 |
| 91 | 200 | 100 | 0 |
| 92 | 200 | 97 | 0 |
| 93 | 200 | 100 | 0 |
| 99 | 200 | 100 | 0 |
| 100 | 200 | 100 | 0 |
| 102 | 200 | 100 | 0 |
| 104 | 200 | 100 | 0 |
| 105 | 200 | 100 | 0 |
| 107 | 200 | 97 | 0 |
| 108 | 200 | 100 | 0 |
| 109 | 200 | 100 | 0 |
| 110 | 200 | 100 | 0 |
| 112 | 200 | 100 | 0 |
| 114 | 200 | 100 | 0 |
| 116 | 200 | 100 | 0 |
| 117 | 200 | 100 | 0 |
| 118 | 200 | 100 | 0 |
| 129 | 200 | 100 | 0 |
| 131 | 200 | 100 | 0 |
| 132 | 200 | 100 | 0 |
| 134 | 200 | 100 | 0 |
| 138 | 200 | 100 | 0 |
| 141 | 200 | 100 | 0 |
| 142 | 200 | 100 | 0 |
| 143 | 200 | 100 | 0 |
| 146 | 200 | 100 | 0 |

TABLE 4-continued

| Compound No. | Concentration of active ingredient (ppm) | Prevention value when inoculated with drug-resistant strain (%) | Prevention value when inoculated with drug-sensitive strain (%) |
|---|---|---|---|
| 155 | 200 | 94 | 0 |
| 157 | 200 | 100 | 0 |
| 160 | 200 | 100 | 0 |
| 164 | 200 | 100 | 0 |
| 168 | 200 | 100 | 0 |
| 181 | 200 | 100 | 0 |
| 188 | 200 | 100 | 0 |
| 193 | 200 | 100 | 0 |
| Control (a) | 200 | 0 | 0 |
| Control (b) | 200 | 0 | 0 |
| Control (c) | 200 | 0 | 0 |
| Control (d) | 200 | 0 | 0 |
| Control (e) | 200 | 0 | 0 |
| Control (f) | 200 | 0 | 0 |
| Control (g) | 200 | 0 | 0 |
| Control (h) | 200 | 0 | 0 |
| Control (i) | 200 | 0 | 0 |
| Control (j) | 200 | 0 | 0 |
| Control (k) | 200 | 0 | 0 |
| Control (l) | 200 | 0 | 0 |
| Swep | 200 | 0 | 0 |
| Chlorpropham | 200 | 0 | 0 |
| Barban | 200 | 34 | 0 |
| CEPC | 200 | 0 | 0 |
| Propham | 200 | 0 | 0 |
| Chlorbufam | 200 | 0 | 0 |
| Benomyl | 200 | 0 | 100 |
| Thiophanate-methyl | 200 | 0 | 100 |
| Carbendazim | 200 | 0 | 100 |

As understood from the results shown in Table 4, the N-phenylcarbamates (I) of the invention show an excellent preventive effect on the drug-resistant strain but do not show any preventive effect on the tested drug-sensitive strain. To the contrary, commecially available known fungicides such as Benomyl and Thiophanate-methyl show a notable controlling effect on the drug-sensitive strain but not on the drug-resistant strain. Other tested compounds structurally similar to the N-phenylcarbamates (I) do not show any fungicidal activity on the drug-sensitive strain and the drug-resistant strain.

Experiment 3

Preventive effect on scab of pear (*Venturia nashicola*):

A plastic pot of 90 ml volume was filled with sandy soil, and seeds of pear (var: Chojuro) were sown therein. Cultivation was carried out in a greenhouse for 20 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Venturia nashicola* by spraying. The resulting plants were placed at 20° C. under a condition of high humidity for 3 days and then at 20° C. under irradiation with a fluorescent lamp for 20 days. The degree of damage was determined in the same manner as in Experiment 1, and the results are shown in Table 5.

TABLE 5

| Compound No. | Concentration of active ingredient (ppm) | Prevention value when inoculated with drug-resistant strain (%) | Prevention value when inoculated with drug-sensitive strain (%) |
|---|---|---|---|
| 2 | 200 | 100 | 0 |
| 3 | 200 | 94 | 0 |
| 5 | 200 | 91 | 0 |
| 8 | 200 | 97 | 0 |
| 9 | 200 | 96 | 0 |
| 10 | 200 | 94 | 0 |
| 13 | 200 | 100 | 0 |
| 14 | 200 | 91 | 0 |
| 15 | 200 | 100 | 0 |
| 19 | 200 | 100 | 0 |
| 20 | 200 | 100 | 0 |
| 22 | 200 | 100 | 0 |
| 24 | 200 | 100 | 0 |
| 26 | 200 | 91 | 0 |
| 27 | 200 | 88 | 0 |
| 29 | 200 | 100 | 0 |
| 30 | 200 | 88 | 0 |
| 31 | 200 | 100 | 0 |
| 35 | 200 | 88 | 0 |
| 38 | 200 | 100 | 0 |
| 42 | 200 | 85 | 0 |
| 43 | 200 | 88 | 0 |
| 44 | 200 | 100 | 0 |
| 45 | 200 | 91 | 0 |
| 46 | 200 | 94 | 0 |
| 47 | 200 | 100 | 0 |
| 48 | 200 | 94 | 0 |
| 49 | 200 | 85 | 0 |
| 51 | 200 | 94 | 0 |
| 53 | 200 | 100 | 0 |
| 55 | 200 | 100 | 0 |
| 64 | 200 | 100 | 0 |
| 65 | 200 | 100 | 0 |
| 68 | 200 | 100 | 0 |
| 81 | 200 | 97 | 0 |
| 87 | 200 | 94 | 0 |
| 89 | 200 | 88 | 0 |
| 98 | 200 | 100 | 0 |
| 100 | 200 | 100 | 0 |
| 102 | 200 | 100 | 0 |
| 103 | 200 | 100 | 0 |
| 104 | 200 | 100 | 0 |
| 105 | 200 | 100 | 0 |
| 106 | 200 | 100 | 0 |
| 107 | 200 | 91 | 0 |
| 108 | 200 | 100 | 0 |
| 110 | 200 | 100 | 0 |
| 112 | 200 | 100 | 0 |
| 116 | 200 | 100 | 0 |
| 117 | 200 | 100 | 0 |
| 118 | 200 | 100 | 0 |
| 124 | 200 | 100 | 0 |
| 128 | 200 | 100 | 0 |
| 132 | 200 | 100 | 0 |
| 134 | 200 | 100 | 0 |
| 138 | 200 | 100 | 0 |
| 141 | 200 | 100 | 0 |
| 143 | 200 | 100 | 0 |
| 145 | 200 | 100 | 0 |
| 146 | 200 | 100 | 0 |
| 153 | 200 | 97 | 0 |
| 156 | 200 | 100 | 0 |
| 163 | 200 | 100 | 0 |
| 164 | 200 | 100 | 0 |
| 174 | 200 | 100 | 0 |
| 181 | 200 | 100 | 0 |
| Benomyl | 200 | 0 | 100 |
| Thiophanate-methyl | 200 | 0 | 100 |

As understood from the results shown in Table 5, the N-phenylcarbamates (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

Experiment 4

Preventive effect on brown leaf-spot of peanut (*Cercospora arachidicola*):

A plastic pot of 90 ml volume was filled with sandy soil, and seeds of peanut (var: Chiba hanryusei) were sown therein. Cultivation was carried out in a greenhouse for 14 days. Onto the resulting seedlings, the test compound formulated in emulsifiable concentrate or wettable powder and diluted with water was sprayed at a rate of 10 ml per pot. Then, the seedlings were inoculated with a spore suspension of the drug-resistant or drug-sensitive strain of *Cercospora arachidicola* by spraying. The resulting plants were covered with a polyvinyl chloride sheet to make a condition of humidity and cultivated in the greenhouse for 10 days. The degree of damage was determined in the same manner as in Experiment 1, and the results are shown in Table 6.

TABLE 6

| Compound No. | Concentration of active ingredient (ppm) | Prevention value when inoculated with drug-resistant strain (%) | Prevention value when inoculated with drug-sensitive strain (%) |
|---|---|---|---|
| 2 | 200 | 100 | 0 |
| 6 | 200 | 100 | 0 |
| 7 | 200 | 100 | 0 |
| 8 | 200 | 100 | 0 |
| 10 | 200 | 100 | 0 |
| 12 | 200 | 97 | 0 |
| 15 | 200 | 100 | 0 |
| 19 | 200 | 100 | 0 |
| 20 | 200 | 98 | 0 |
| 22 | 200 | 100 | 0 |
| 24 | 200 | 98 | 0 |
| 29 | 200 | 100 | 0 |
| 32 | 200 | 100 | 0 |
| 36 | 200 | 100 | 0 |
| 38 | 200 | 94 | 0 |
| 41 | 200 | 100 | 0 |
| 44 | 200 | 97 | 0 |
| 52 | 200 | 97 | 0 |
| 54 | 200 | 100 | 0 |
| 55 | 200 | 100 | 0 |
| 56 | 200 | 100 | 0 |
| 64 | 200 | 100 | 0 |
| 68 | 200 | 100 | 0 |
| 73 | 200 | 100 | 0 |
| 79 | 200 | 100 | 0 |
| 80 | 200 | 100 | 0 |
| 86 | 200 | 94 | 0 |
| 87 | 200 | 91 | 0 |
| 88 | 200 | 100 | 0 |
| 90 | 200 | 100 | 0 |
| 91 | 200 | 100 | 0 |
| 92 | 200 | 100 | 0 |
| 101 | 200 | 100 | 0 |
| 102 | 200 | 100 | 0 |
| 105 | 200 | 100 | 0 |
| 109 | 200 | 100 | 0 |
| 110 | 200 | 100 | 0 |
| 117 | 200 | 100 | 0 |
| 132 | 200 | 100 | 0 |
| 134 | 200 | 100 | 0 |
| 138 | 200 | 100 | 0 |
| 141 | 200 | 100 | 0 |
| 142 | 200 | 100 | 0 |
| 146 | 200 | 100 | 0 |
| 165 | 200 | 100 | 0 |
| 181 | 200 | 100 | 0 |
| Benomyl | 200 | 0 | 100 |

TABLE 6-continued

| Compound No. | Concentration of active ingredient (ppm) | Prevention value when inoculated with drug-resistant strain (%) | Prevention value when inoculated with drug-sensitive strain (%) |
|---|---|---|---|
| Thiophanate-methyl | 200 | 0 | 100 |

As understood from the results shown in Table 6, the N-phenylcarbamates (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

Experiment 5

Preventive effect on gray mold of cucumber (*Botrytis cinerea*):

Plastic pots of 90 ml volume was filled with sandy soil, and seeds of cucumber (var: Sagami-hanjiro) were sown therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Botrytis cinerea* by putting them on the leaf surfaces. After the plants were infected by incubating under high humidity at 20° C. for 3 days, the rates of disease severity were observed. The degree of damage was determined in the same manner as in Experiment 1, and the results are shown in Table 7.

TABLE 7

| Compound No. | Concentration of active ingredient (ppm) | Prevention value when inoculated with drug-resistant strain (%) | Prevention value when inoculated with drug-sensitive strain (%) |
|---|---|---|---|
| 1 | 200 | 88 | 0 |
| 2 | 200 | 100 | 0 |
| 3 | 200 | 94 | 0 |
| 4 | 200 | 88 | 0 |
| 5 | 200 | 91 | 0 |
| 6 | 200 | 96 | 0 |
| 7 | 200 | 100 | 0 |
| 8 | 200 | 97 | 0 |
| 9 | 200 | 91 | 0 |
| 10 | 200 | 97 | 0 |
| 11 | 200 | 84 | 0 |
| 12 | 200 | 100 | 0 |
| 13 | 200 | 96 | 0 |
| 14 | 200 | 88 | 0 |
| 15 | 200 | 100 | 0 |
| 16 | 500 | 91 | 0 |
| 17 | 500 | 88 | 0 |
| 18 | 500 | 88 | 0 |
| 19 | 200 | 100 | 0 |
| 20 | 200 | 100 | 0 |
| 21 | 200 | 97 | 0 |
| 22 | 200 | 100 | 0 |
| 23 | 200 | 88 | 0 |
| 24 | 200 | 100 | 0 |
| 25 | 200 | 97 | 0 |
| 28 | 200 | 97 | 0 |
| 29 | 200 | 100 | 0 |
| 31 | 200 | 94 | 0 |
| 32 | 200 | 97 | 0 |
| 33 | 200 | 88 | 0 |
| 34 | 200 | 84 | 0 |
| 35 | 200 | 91 | 0 |
| 36 | 200 | 97 | 0 |
| 37 | 200 | 91 | 0 |
| 38 | 200 | 94 | 0 |
| 39 | 200 | 94 | 0 |
| 40 | 200 | 97 | 0 |
| 41 | 200 | 100 | 0 |
| 44 | 200 | 94 | 0 |
| 47 | 200 | 91 | 0 |
| 48 | 200 | 88 | 0 |
| 50 | 200 | 94 | 0 |
| 51 | 200 | 91 | 0 |
| 52 | 200 | 97 | 0 |
| 53 | 200 | 100 | 0 |
| 54 | 200 | 100 | 0 |
| 55 | 200 | 100 | 0 |
| 56 | 200 | 100 | 0 |
| 57 | 200 | 100 | 0 |
| 58 | 200 | 100 | 0 |
| 59 | 200 | 97 | 0 |
| 60 | 200 | 100 | 0 |
| 61 | 200 | 88 | 0 |
| 62 | 200 | 100 | 0 |
| 63 | 200 | 100 | 0 |
| 64 | 200 | 100 | 0 |
| 65 | 200 | 100 | 0 |
| 66 | 200 | 100 | 0 |
| 67 | 200 | 100 | 0 |
| 68 | 200 | 100 | 0 |
| 69 | 200 | 100 | 0 |
| 70 | 200 | 100 | 0 |
| 71 | 200 | 100 | 0 |
| 72 | 200 | 100 | 0 |
| 73 | 200 | 100 | 0 |
| 74 | 200 | 100 | 0 |
| 75 | 200 | 100 | 0 |
| 76 | 200 | 100 | 0 |
| 77 | 200 | 100 | 0 |
| 78 | 200 | 100 | 0 |
| 79 | 200 | 100 | 0 |
| 80 | 200 | 100 | 0 |
| 81 | 200 | 94 | 0 |
| 82 | 200 | 100 | 0 |
| 83 | 200 | 100 | 0 |
| 84 | 200 | 100 | 0 |
| 85 | 200 | 100 | 0 |
| 86 | 200 | 100 | 0 |
| 88 | 200 | 97 | 0 |
| 90 | 200 | 100 | 0 |
| 91 | 200 | 100 | 0 |
| 92 | 200 | 97 | 0 |
| 93 | 200 | 94 | 0 |
| 94 | 200 | 97 | 0 |
| 95 | 200 | 88 | 0 |
| 96 | 200 | 100 | 0 |
| 97 | 200 | 100 | 0 |
| 98 | 200 | 91 | 0 |
| 99 | 200 | 97 | 0 |
| 100 | 200 | 100 | 0 |
| 101 | 200 | 100 | 0 |
| 102 | 200 | 100 | 0 |
| 103 | 200 | 97 | 0 |
| 104 | 200 | 100 | 0 |
| 105 | 200 | 100 | 0 |
| 106 | 200 | 100 | 0 |
| 107 | 200 | 91 | 0 |
| 108 | 200 | 100 | 0 |
| 109 | 200 | 100 | 0 |
| 110 | 200 | 100 | 0 |
| 111 | 200 | 100 | 0 |
| 112 | 200 | 100 | 0 |
| 113 | 200 | 100 | 0 |
| 114 | 200 | 100 | 0 |

TABLE 7-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| 115 | 200 | 100 | 0 |
| 116 | 200 | 100 | 0 |
| 117 | 200 | 100 | 0 |
| 118 | 200 | 100 | 0 |
| 119 | 200 | 100 | 0 |
| 120 | 200 | 100 | 0 |
| 121 | 200 | 100 | 0 |
| 122 | 200 | 88 | 0 |
| 123 | 200 | 100 | 0 |
| 124 | 200 | 100 | 0 |
| 125 | 200 | 94 | 0 |
| 126 | 200 | 94 | 0 |
| 127 | 200 | 100 | 0 |
| 128 | 200 | 100 | 0 |
| 129 | 200 | 100 | 0 |
| 130 | 200 | 100 | 0 |
| 131 | 200 | 100 | 0 |
| 132 | 200 | 100 | 0 |
| 133 | 200 | 100 | 0 |
| 134 | 200 | 100 | 0 |
| 135 | 200 | 100 | 0 |
| 136 | 200 | 100 | 0 |
| 137 | 200 | 100 | 0 |
| 138 | 200 | 100 | 0 |
| 139 | 200 | 100 | 0 |
| 140 | 200 | 100 | 0 |
| 141 | 200 | 100 | 0 |
| 142 | 200 | 100 | 0 |
| 143 | 200 | 100 | 0 |
| 144 | 200 | 100 | 0 |
| 145 | 200 | 100 | 0 |
| 146 | 200 | 100 | 0 |
| 147 | 200 | 100 | 0 |
| 148 | 200 | 100 | 0 |
| 149 | 200 | 100 | 0 |
| 150 | 200 | 100 | 0 |
| 151 | 200 | 100 | 0 |
| 152 | 200 | 100 | 0 |
| 153 | 200 | 97 | 0 |
| 154 | 200 | 88 | 0 |
| 155 | 200 | 91 | 0 |
| 156 | 200 | 97 | 0 |
| 157 | 200 | 100 | 0 |
| 158 | 200 | 100 | 0 |
| 159 | 200 | 100 | 0 |
| 160 | 200 | 100 | 0 |
| 161 | 200 | 100 | 0 |
| 162 | 200 | 100 | 0 |
| 163 | 200 | 100 | 0 |
| 164 | 200 | 100 | 0 |
| 165 | 200 | 100 | 0 |
| 166 | 200 | 100 | 0 |
| 167 | 200 | 100 | 0 |
| 168 | 200 | 100 | 0 |
| 169 | 200 | 100 | 0 |
| 170 | 200 | 94 | 0 |
| 171 | 200 | 100 | 0 |
| 172 | 200 | 100 | 0 |
| 173 | 200 | 100 | 0 |
| 174 | 200 | 100 | 0 |
| 175 | 200 | 100 | 0 |
| 176 | 200 | 100 | 0 |
| 177 | 500 | 88 | 0 |
| 178 | 500 | 88 | 0 |
| 179 | 500 | 88 | 0 |
| 180 | 200 | 100 | 0 |
| 181 | 200 | 100 | 0 |
| 182 | 200 | 100 | 0 |
| 183 | 200 | 100 | 0 |
| 184 | 200 | 100 | 0 |
| 185 | 200 | 94 | 0 |
| 186 | 200 | 88 | 0 |
| 187 | 200 | 100 | 0 |
| 188 | 200 | 100 | 0 |
| 189 | 200 | 100 | 0 |
| 190 | 200 | 100 | 0 |
| 191 | 200 | 100 | 0 |
| 192 | 200 | 100 | 0 |
| 193 | 200 | 100 | 0 |
| 194 | 200 | 100 | 0 |
| 195 | 200 | 100 | 0 |
| 196 | 200 | 100 | 0 |
| 197 | 200 | 97 | 0 |
| 198 | 200 | 94 | 0 |
| 199 | 200 | 100 | 0 |
| 200 | 200 | 100 | 0 |
| 201 | 200 | 100 | 0 |
| 202 | 200 | 100 | 0 |
| 203 | 200 | 100 | 0 |
| 204 | 200 | 100 | 0 |
| 205 | 200 | 100 | 0 |
| 206 | 200 | 100 | 0 |
| 207 | 200 | 88 | 0 |
| 208 | 200 | 100 | 0 |
| 209 | 200 | 100 | 0 |
| Benomyl | 200 | 0 | 100 |
| Thiophanate-methyl | 200 | 0 | 100 |

As understood from the results shown in Table 7, the N-phenylcarbamates (I) of the invention show an excellent preventive effect on the drug-resistant strain but do not show any preventive effect on the tested drug-sensitive strain. To the contrary, commercially available known fungicides such as Benomyl, Thioophanate-methyl and Carbendazim show a notable controlling effect on the drug-sensitive strain but not on the drug-resistant strain.

Experiment 6

Preventive effect on gummy stem blight of cucumber (*Mycosphaerella melonis*):

Plastic pots of 90 ml volume was filled with sandy soil, and seeds of cucumber (var: Sagami-hanjiro) were sown therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 10 ml per pot. After air-drying, the seedlings were inoculated with mycelial disks (5 mm in diameter) of the drug-resistant or drug-sensitive strain of *Mycosphaerella melonis* by putting them on the leaf surfaces. After the plants were infected by incubating under high humidity at 25° C. for 4 days, the rates of disease severity were observed. The degree of damage was determined in the same manner as in Experiment 1, and the results are shown in Table 8.

TABLE 8

| Compound No. | Concentration of active ingredient (ppm) | Prevention value when inoculated with drug-resistant strain (%) | Prevention value when inoculated with drug-sensitive strain (%) |
| --- | --- | --- | --- |
| 2 | 200 | 100 | 0 |
| 6 | 200 | 100 | 0 |
| 7 | 200 | 100 | 0 |
| 8 | 200 | 100 | 0 |
| 10 | 200 | 100 | 0 |
| 15 | 200 | 100 | 0 |
| 19 | 200 | 100 | 0 |

TABLE 8-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| 20 | 200 | 100 | 0 |
| 22 | 200 | 100 | 0 |
| 23 | 200 | 91 | 0 |
| 29 | 200 | 100 | 0 |
| 31 | 200 | 97 | 0 |
| 36 | 200 | 100 | 0 |
| 39 | 200 | 97 | 0 |
| 40 | 200 | 100 | 0 |
| 54 | 200 | 100 | 0 |
| 56 | 200 | 100 | 0 |
| 57 | 200 | 100 | 0 |
| 59 | 200 | 100 | 0 |
| 64 | 200 | 100 | 0 |
| 68 | 200 | 100 | 0 |
| 77 | 200 | 100 | 0 |
| 78 | 200 | 100 | 0 |
| 79 | 200 | 100 | 0 |
| 80 | 200 | 100 | 0 |
| 86 | 200 | 100 | 0 |
| 88 | 200 | 97 | 0 |
| 90 | 200 | 100 | 0 |
| 91 | 200 | 100 | 0 |
| 101 | 200 | 100 | 0 |
| 102 | 200 | 100 | 0 |
| 105 | 200 | 100 | 0 |
| 109 | 200 | 100 | 0 |
| 110 | 200 | 100 | 0 |
| 117 | 200 | 100 | 0 |
| 124 | 200 | 100 | 0 |
| 132 | 200 | 100 | 0 |
| 134 | 200 | 100 | 0 |
| 138 | 200 | 100 | 0 |
| 141 | 200 | 100 | 0 |
| 142 | 200 | 100 | 0 |
| 146 | 200 | 100 | 0 |
| 181 | 200 | 100 | 0 |
| Benomyl | 200 | 0 | 100 |
| Thiophanate-methyl | 200 | 0 | 100 |

As understood from the results shown in Table 8, the N-phenylcarbamates (I) of the invention show an excellent preventive effect on the drug-resistant strain but do not show any preventive effect on the tested drug-sensitive strain. To the contrary, commercially available known fungicides such as Benomyl and Thiophanate-methyl show a notable controlling effect on the drug-sensitive strain but not on the drug-resistant strain.

Experiment 7

Preventive effect on green mold of orange (*Penicillium italicum*):

Fruits of orange (var: Unshu) were washed with water and dried in the air. The fruits were immersed in a solution of the test compound prepared by diluting an emulsifiable concentrate comprising the test compound with water for 1 minute. After drying in the air, the fruits were inoculated with a spore suspension of the drug-resistant or drug-sensitive strain of *Pencillium italicum* by spraying and placed in a room of high humidity for 14 days. The degree of damage was determined in the following manner:

The fruits examined were measured for a percentage of infected area and classified into the corresponding indices, 0, 1, 2, 3, 4, 5:

| Disease index | Percentage of infected area |
| --- | --- |
| 0 | No infection |
| 1 | Infected area of less than 20% |
| 2 | Infected area of less than 40% |
| 3 | Infected area of less than 60% |
| 4 | Infected area of less than 80% |
| 5 | Infected area of not less than 80% |

Calculation of the degree of damage and the prevention value was made as in Experiment 1.

The results are shown in Table 9.

TABLE 9

| Compound No. | Concentration of active ingredient (ppm) | Prevention value when inoculated with drug-resistant strain (%) | Prevention value when inoculated with drug-sensitive strain (%) |
| --- | --- | --- | --- |
| 2 | 200 | 100 | 0 |
| 6 | 200 | 100 | 0 |
| 7 | 200 | 100 | 0 |
| 8 | 200 | 100 | 0 |
| 13 | 200 | 100 | 0 |
| 15 | 200 | 100 | 0 |
| 19 | 200 | 100 | 0 |
| 20 | 200 | 100 | 0 |
| 22 | 200 | 100 | 0 |
| 24 | 200 | 100 | 0 |
| 28 | 200 | 100 | 0 |
| 29 | 200 | 100 | 0 |
| 36 | 200 | 100 | 0 |
| 38 | 200 | 94 | 0 |
| 40 | 200 | 97 | 0 |
| 51 | 200 | 100 | 0 |
| 55 | 200 | 100 | 0 |
| 56 | 200 | 100 | 0 |
| 64 | 200 | 100 | 0 |
| 68 | 200 | 100 | 0 |
| 73 | 200 | 100 | 0 |
| 78 | 200 | 100 | 0 |
| 79 | 200 | 100 | 0 |
| 90 | 200 | 100 | 0 |
| 99 | 200 | 100 | 0 |
| 103 | 200 | 100 | 0 |
| 109 | 200 | 100 | 0 |
| 110 | 200 | 100 | 0 |
| 116 | 200 | 100 | 0 |
| 117 | 200 | 100 | 0 |
| 118 | 200 | 100 | 0 |
| 129 | 200 | 100 | 0 |
| 132 | 200 | 100 | 0 |
| 134 | 200 | 100 | 0 |
| 138 | 200 | 100 | 0 |
| 141 | 200 | 100 | 0 |
| 146 | 200 | 100 | 0 |
| 156 | 200 | 100 | 0 |
| 163 | 200 | 94 | 0 |
| 181 | 200 | 100 | 0 |
| Benomyl | 200 | 0 | 100 |
| Thiophanate-methyl | 200 | 0 | 100 |
| Thiabendazole | 200 | 0 | 100 |

As understood from the results shown in Table 9, the N-phenylcarbamates (I) of the invention show an excellent preventive effect on the drug-resistant strain but do not show any preventive effect on the tested drug-sensitive strain. To the contrary, commercially available known fungicides such as Benomyl, Thiophanate-methyl and Thiabendazole show a notable controlling effect on the drug-sensitive strain but not on the drug-resistant strain.

Experiment 8

Preventive effect on rice blast (*Pyricularia oryzae*):

Plastic pots of 90 ml volume were filled with a cultured soil for rice plants, and seeds of rice plant (var: Kinki No. 33) were sowed therein and cultivated in a greenhouse. Onto the seedlings of 3-leaf stage, the test compound formulated in an emulsifiable concentrate and diluted with water was sprayed to enough cover the leaf surfaces with droplets. After air-drying, the seedlings were inoculated with a spore suspension of *Pyricularia oryzae* by spraying, followed by incubation at 28° C. for 3 days under a high humid condition. The disease severity were observed and the degree of damage was determined in the same manner as in Experiment 1. The results are shown in Table 10.

TABLE 10

| Compound No. | Concentration of active ingredient (ppm) | Prevention value (%) |
| --- | --- | --- |
| 28 | 500 | 100 |
| 46 | 500 | 100 |
| 47 | 500 | 100 |
| 101 | 500 | 97 |
| 153 | 1000 | 99 |
| 154 | 1000 | 95 |
| Edifenphos | 500 | 97 |

Experiment 9

Phytotoxicity on crop plants:

Plastic pots of 150 ml volume were filled with sandy soil, and seeds of wheat (var: Norin No. 61), apple (var: Kogyoku) and peanut (var: Chiba hanryusei) were sown therein. Cultivation was carried out in a greenhouse. Onto the resulting seedlings, the test compound formulated in emulsifiable concentrate or wettable powder and diluted with water was sprayed. After cultivation in the greenhouse for additional 10 days, the phytotoxicity was examined on the following criteria:

| Extent | Observation |
| --- | --- |
| − | No abnormality |
| + | Abnormality due to phytotoxicity observed in a part of crop plants |
| ++ | Abnormality due to phytotoxicity observed in entire crop plants |
| +++ | Crop plants withered due to phytotoxicity |

The results are shown in Table 11.

TABLE 11

| Compound No. | Concentration of active ingredient (ppm) | Phytotoxicity Wheat | Phytotoxicity Apple | Phytotoxicity Peanut |
| --- | --- | --- | --- | --- |
| 2 | 1000 | − | − | − |
| 15 | 1000 | − | − | − |
| 28 | 1000 | − | − | − |
| 39 | 1000 | − | − | − |
| 59 | 1000 | − | − | − |
| 79 | 1000 | − | − | − |
| 102 | 1000 | − | − | − |
| 108 | 1000 | − | − | − |
| 109 | 1000 | − | − | − |
| 110 | 1000 | − | − | − |
| 117 | 1000 | − | − | − |
| 120 | 1000 | − | − | − |
| 141 | 1000 | − | − | − |
| 145 | 1000 | − | − | − |
| 153 | 1000 | − | − | − |
| Barban | 1000 | − | ++ | ++ |
| CEPC | 1000 | − | ++ | ++ |
| Swep | 1000 | ++ | ++ | + |

As understood from the results shown in Table 11, the N-phenylcarbamates (I) of the invention produce no material phytotoxicity, while commercially available herbicides having a chemical structure similar thereto produce considerable phytotoxicity.

Experiment 10

Preventive effect on powdery mildew of cucumber (*Sphaerotheca fuliginea*):

A plastic pot of 90 ml volume was filled with sandy soil, and seeds of cucumber (var: Sagami-hanjiro) were sown therein. Cultivation was carried out in a greenhouse for 8 days. Onto the resulting seedlings having cotyledons, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Sphaerotheca fuliginea* by spraying and further cultivated in the greenhouse. Ten days thereafter, the infectious state of the plants was observed. The degree of damage was determined in the same manner as in Experiment 1, and the results are shown in Table 12.

TABLE 12

| Compound No. | Concentration of active ingredient (ppm) | Prevention value (%) |
| --- | --- | --- |
| 2 | 100 | 36 |
| 2 | 20 | 0 |
| 15 | 100 | 32 |
| 15 | 20 | 0 |
| 22 | 100 | 44 |
| 22 | 20 | 0 |
| 54 | 100 | 28 |
| 54 | 20 | 0 |
| 59 | 100 | 36 |
| 59 | 20 | 0 |
| 105 | 100 | 28 |
| 105 | 20 | 0 |
| 110 | 100 | 32 |
| 110 | 20 | 0 |
| 117 | 100 | 36 |
| 117 | 20 | 0 |
| 141 | 100 | 28 |
| 141 | 20 | 0 |
| 181 | 100 | 44 |
| 181 | 20 | 0 |
| A | 100 | 45 |
| A | 20 | 12 |
| B | 500 | 42 |
| B | 100 | 10 |
| C | 100 | 42 |
| C | 20 | 8 |
| D | 500 | 36 |
| D | 100 | 0 |
| E | 100 | 44 |
| E | 20 | 10 |
| F | 100 | 43 |
| F | 20 | 8 |
| G | 100 | 42 |
| G | 20 | 8 |
| H | 100 | 40 |
| H | 20 | 5 |
| 2 + A | 20 + 20 | 100 |
| 2 + F | 20 + 20 | 100 |

TABLE 12-continued

| Compound No. | Concentration of active ingredient (ppm) | Prevention value (%) |
|---|---|---|
| 15 + A | 20 + 20 | 100 |
| 15 + F | 20 + 20 | 100 |
| 22 + A | 20 + 20 | 100 |
| 22 + B | 20 + 20 | 100 |
| 22 + C | 20 + 20 | 100 |
| 22 + D | 20 + 20 | 100 |
| 54 + G | 20 + 20 | 100 |
| 54 + H | 20 + 20 | 100 |
| 59 + A | 20 + 20 | 100 |
| 59 + B | 20 + 20 | 100 |
| 59 + E | 20 + 20 | 100 |
| 59 + F | 20 + 20 | 100 |
| 105 + A | 20 + 20 | 100 |
| 105 + E | 20 + 20 | 100 |
| 110 + E | 20 + 20 | 100 |
| 110 + F | 20 + 20 | 100 |
| 117 + G | 20 + 20 | 100 |
| 117 + H | 20 + 20 | 100 |
| 141 + A | 20 + 20 | 100 |
| 141 + B | 20 + 20 | 100 |
| 181 + A | 20 + 20 | 100 |
| 181 + B | 20 + 20 | 100 |
| 181 + E | 20 + 20 | 100 |
| 181 + F | 20 + 20 | 100 |

As understood from the results shown in Table 12, the combined use of the N-phenylcarbamates (I) of the invention with benzimidazole thiophanate fungicides and/or cyclic imide fungicides show much more excellent preventive effect than their sole use.

Experiment 11

Preventive effect on gray mold of tomato (*Botrytis cinerea*):

A plastic pot of 90 ml volume was filled with sandy soil, and seeds of tomato (var: Fukuji No. 2) were sown therein. Cultivation was carried out in a greenhouse for 4 weeks. Onto the resulting seedlings at the 4-leaf stage, the test compound(s) formulated in emulsifiable concentrate or wettable powder and diluted with water were sprayed at a rate of 10 ml per pot. Then, the seedlings were inoculated with a mixed spore suspension of the drug-resistant and drug-sensitive strain of *Botrytis cinerea* by spraying and placed at 20° C. in a room of high humidity for 5 days. The degree of damage was determined in the same manner as in Experiment 1, and the results are shown in Table 13.

TABLE 13

| Compound No. | Concentration of active ingredient (ppm) | Prevention value (%) |
|---|---|---|
| 2 | 100 | 42 |
| 2 | 20 | 0 |
| 15 | 100 | 32 |
| 15 | 20 | 0 |
| 22 | 100 | 38 |
| 22 | 20 | 0 |
| 54 | 100 | 40 |
| 54 | 20 | 0 |
| 59 | 100 | 32 |
| 59 | 20 | 0 |
| 105 | 100 | 38 |
| 105 | 20 | 0 |
| 110 | 100 | 40 |
| 110 | 20 | 0 |
| 117 | 100 | 38 |
| 117 | 20 | 0 |
| 141 | 100 | 42 |
| 141 | 20 | 0 |
| 181 | 100 | 28 |
| 181 | 20 | 0 |

TABLE 13-continued

| Compound No. | Concentration of active ingredient (ppm) | Prevention value (%) |
|---|---|---|
| I | 100 | 48 |
| I | 20 | 22 |
| J | 500 | 46 |
| J | 100 | 18 |
| K | 100 | 42 |
| K | 20 | 15 |
| L | 500 | 42 |
| L | 100 | 12 |
| 2 + I | 20 + 50 | 100 |
| 2 + J | 20 + 50 | 100 |
| 2 + K | 20 + 50 | 100 |
| 2 + L | 20 + 50 | 100 |
| 15 + I | 20 + 50 | 100 |
| 15 + K | 20 + 50 | 100 |
| 22 + I | 20 + 50 | 100 |
| 22 + L | 20 + 50 | 100 |
| 54 + I | 20 + 50 | 100 |
| 54 + J | 20 + 50 | 100 |
| 59 + I | 20 + 50 | 100 |
| 59 + K | 20 + 50 | 100 |
| 105 + I | 20 + 50 | 100 |
| 105 + J | 20 + 50 | 100 |
| 110 + I | 20 + 50 | 100 |
| 110 + J | 20 + 50 | 100 |
| 117 + I | 20 + 50 | 100 |
| 117 + K | 20 + 50 | 100 |
| 141 + I | 20 + 50 | 100 |
| 141 + J | 20 + 50 | 100 |
| 181 + I | 20 + 50 | 100 |
| 181 + K | 20 + 50 | 100 |

As understood from the results shown in Table 13, the combined use of the N-phenylcarbamates (I) of the invention with benzimidazole thiophanate fungicides and/or cyclic imide fungicides show much more excellent preventive effect than their sole use.

What is claimed is:

1. An N-phenylcarbamate of the formula:

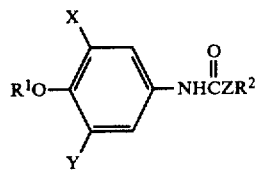

wherein X and Y, which may be the same or different, are each a halogen atom, a lower alkyl group, a lower alkenyl group, a lower cyanoalkenyl group, a lower alkynyl group, a lower alkoxy group, a cyano group, a lower alkyl group substituted with at least one member selected from the group consisting of halogen, hydroxyl and cyano, or a group of the formula:

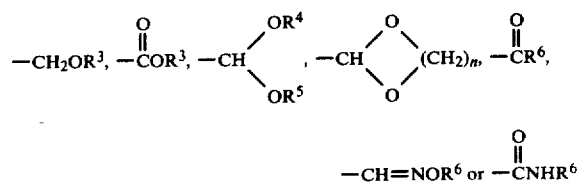

$$-CH=NOR^6 \text{ or } -\overset{O}{\underset{\|}{C}}NHR^6$$

in which $R^3$ is a lower alkyl group, a lower alkenyl group, a lower alkynyl group or a lower haloalkyl group, $R^4$ and $R^5$, which may be the same or different, are each a lower alkyl group, $R^6$ is a hydrogen atom or a lower alkyl group, n is 2, 3 or 4, Z is an oxygen atom or a sulfur atom, $R^1$ is a lower alkyl group, a lower alkenyl group, a lower alkynyl group or a lower alkyl group substituted with at least one member selected from the group consisting of halogen, lower alkoxy and lower cycloalkyl and $R^2$ is a $C_1$–$C_8$ alkyl group, a $C_3$–$C_8$ alkenyl group, a $C_3$–$C_8$ alkynyl group, a lower cycloalkyl group, a lower haloalkenyl group, a lower haloalkynyl group or a lower alkyl group substituted with at least one member selected from the group consisting of halogen, cyano, lower alkoxy, lower alkenyloxy, lower haloalkoxy, phenoxy, lower aralkyloxy and lower cycloalkyl, with the proviso that ethyl N-(3,4,5-trimethoxy)phenylcarbamate, ethyl N-(3,4,5-triethoxy)phenylcarbamate 2-butynyl N-C3,4,5-trimethoxyphenyl)carbamate and propargyl N-(3,5-dibromo-4-methoxy)phenylcarbamate are not included and with the further proviso that when Z is sulfur and X and Y are each halogen, $R_1$ and $R_2$ are not both methyl.

2. The N-phenylcarbamate according to claim 1, wherein X and Y are independently fluorine, chlorine, bromine, iodine, methyl, ethyl, n-propyl, n-butyl, vinyl, 1-propenyl, 2-propenyl, ethynyl, methoxy, ethoxy, cyano, 1,2-dibromoethyl, hydroxymethyl, cyanomethyl, 2-cyanoethyl, 2-cyanovinyl, methoxymethyl, ethoxymethyl, allyloxymethyl, propargyloxymethyl, 2-fluoroethoxymethyl, methoxycarbonyl, ethoxycarbonyl, allyloxycarbonyl, 2-fluoroethoxycarbonyl, propargyloxycarbonyl, dimethoxymethyl, diethoxymethyl, ethylenedioxymethyl, formyl, acetyl, hydroxyiminomethyl, methoxyiminomethyl, carbamoyl, or N-methylcarbamoyl, Z is oxygen or sulfur, $R^1$ is methyl, ethyl, n-propyl, allyl, 2-butenyl, 3-butenyl, propargyl, 3-butynyl, difluoromethyl, 2-chloroethyl, 2,2,2-trifluoroethyl, 2-methoxyethyl or cyclopropylmethyl and $R^2$ is methyl, ethyl, isopropyl, sec-butyl, allyl, 1-ethylpropyl, 1-methylbutyl, 1-methylpentyl, 1-methylheptyl, 1-methyl-2-propenyl, propargyl, 2-butenyl, 1-methyl-3-butenyl, 1-pentyl-2-propenyl, 1-methyl-2-propynyl, 1-ethyl-2-propynyl, 2-butynyl, 3-butynyl, 1-methyl-3-butynyl, 1-butyl-2-propynyl, 1-pentyl-2-propynyl, cyclobutyl, 2-cyanoethyl, 2-fluoroethyl, 2-chloroethyl, 2-bromoethyl, 2,2,2-trifluoroethyl, 1-fluoromethyl-2-fluoroethyl, 1-chloromethylethyl, 1-bromomethylpropyl, 1-methoxymethyl-2-chloroethyl, 4-chloro-2-butenyl, 4-chloro-2-butynyl, 1-cyclopropylethyl, 1-cyclopentylethyl, 2-methoxyethyl, 2-n-propoxyethyl, 2-isopropoxyethyl, 2-allyloxyethyl, 2-(2-chloroethoxy)ethyl, 2-benzyloxyethyl, 1-methyl-2-methoxyethyl, 1-methyl-2-n-butoxyethyl or 1-methyl-2-phenoxyethyl.

3. The N-phenylcarbamate according to claim 1, wherein X and Y are independently chlorine, bromine, iodine, methyl, ethyl, n-propyl, vinyl, 1-propenyl, 2-propenyl, ethynyl, methoxy, ethoxy, cyano, 1,2-dibromoethyl, methoxymethyl, methoxycarbonyl, dimethoxymethyl, diethoxymethyl, acetyl or methoxyiminomethyl, Z is oxygen, $R^1$ is methyl, ethyl, allyl, propargyl, difluoromethyl or 2-chloroethyl and $R^2$ is methyl, ethyl, isopropyl, sec-butyl, allyl, 1-ethylpropyl, 1-methyl-2-propenyl, 2-butenyl, propargyl, 1-methyl-2-propynyl, 1-ethyl-2-propynyl, 2-butynyl, 1-methyl-3-butynyl, 2-cyanoethyl, 2-fluoroethyl, 1-fluoromethyl-2-fluoroethyl, 1-chloromethylethyl, 1-methoxymethyl-2-chloroethyl, 4-chloro-2-butynyl, 1-cyclopropylethyl, 2-(2-chloroethoxy)ethyl or 1-methyl-2-methoxyethyl or 1-methyl-2-n-butoxyethyl.

4. The N-phenylcarbamate according to claim 1, wherein X and Y are independently chlorine, bromine, methoxymethyl, methyl, ethyl or n-propyl, Z is oxygen, $R^1$ is ethyl, allyl, propargyl or 2-chloroethyl and $R^2$ is methyl, ethyl, isopropyl, sec-butyl, allyl, 1-methyl-2-propenyl, propargyl, 1-methyl-2-propynyl, 2-butynyl, 2-cyanoethyl, 4-chloro-2-butynyl or 1-methyl-2-methoxyethyl.

5. The N-phenylcarbamate according to claim 1, wherein X is methoxy or ethoxy, Y is chlorine, bromine, methyl, ethyl, n-propyl, methoxy, ethoxy, cyano, methoxymethyl, methoxycarbonyl, dimethoxymethyl or acetyl, Z is oxygen, $R^1$ is ethyl, allyl, propargyl or 2-chloroethyl and $R^2$ is methyl, ethyl, isopropyl, sec-butyl, allyl, 1-methyl-2-propenyl, propargyl, 1-methyl-2-propynyl, 2-butynyl, 2-cyanoethyl, 4-chloro-2-butynyl or 1-methyl-2-methoxyethyl.

6. The N-phenylcarbamate according to claim 4, wherein X and Y are independently chlorine, methyl or methoxymethyl.

7. The N-phenylcarbamate according to claim 6, wherein $R^1$ is ethyl.

8. The N-phenylcarbamate according to claim 5, wherein Y is chlorine, methyl, methoxymethyl or cyano.

9. The N-phenylcarbamate according to claim 8, wherein $R^1$ is ethyl.

10. Isopropyl N-(3,5-dichloro-4-ethoxyphenyl)carbamate.

11. Isopropyl N-(3,5-dimethyl-4-ethoxyphenyl)carbamate.

12. Propargyl N-(3,5-dimethyl-4-ethoxyphenyl)carbamate.

13. 1-Methyl-2-propenyl N-(3,5-dimethyl-4-ethoxyphenyl)carbamate.

14. 1-Methyl-2-propynyl N-(3,5-dimethyl-4-ethoxyphenyl)carbamate.

15. 1-Methyl-2-methoxyethyl N-(3,5-dimethyl-4-ethoxyphenyl)carbamate.

16. Isopropyl N-[3,5-dimethyl-4-(2-propynyloxy)phenyl]carbamate.

17. Isopropyl N-(3-chloro-4-ethoxy-5-methoxyphenyl)carbamate.

18. Methyl N-(3-chloro-4,5-diethoxyphenyl)carbamate.

19. Ethyl N-(3-chloro-4,5-diethoxyphenyl)carbamate.

20. Isopropyl N-(3-chloro-4,5-diethoxyphenyl)carbamate.

21. sec-Butyl N-(3-chloro-4,5-diethoxyphenyl)carbamate.

22. Allyl N-(3-chloro-4,5-diethoxyphenyl)carbamate.

23. Propargyl N-(3-chloro-4,5-diethoxyphenyl)carbamate.

24. 1-Methyl-2-propenyl N-(3-chloro-4,5-diethoxyphenyl)carbamate.

25. 1-Methyl-2-propynyl N-(3-chloro-4,5-diethoxyphenyl)carbamate.

26. 4-Chloro-2-butynyl N-(3-chloro-4,5-diethoxyphenyl)carbamate.

27. 2-Cyanoethyl N-(3-chloro-4,5-diethoxyphenyl)carbamate.

28. Isopropyl N-[3-chloro-5-ethoxy-4-(2-propenyloxy)phenyl]carbamate.

29. 1-Methyl-2-methoxyethyl N-[3-chloro-5-ethoxy-4-(2-propenyloxy)phenyl]carbamate.

30. Isopropyl N-[3-chloro-5-ethoxy-4-(2-propynyloxy)phenyl]carbamate.

31. Isopropyl N-[3-chloro-4-(2-chloroethyloxy)-5-ethoxyphenyl]carbamate.

32. Isopropyl N-(3-methoxy-4-ethoxy-5-methylphenyl)carbamate.
33. Methyl N-(3,4-diethoxy-5-methylphenyl)carbamate.
34. Ethyl N-(3,4-diethoxy-5-methylphenyl)carbamate.
35. Isopropyl N-(3,4-diethoxy-5-methylphenyl)carbamate.
36. sec-Butyl N-(3,4-diethoxy-5-methylphenyl)carbamate.
37. Propargyl N-(3,4-diethoxy-5-methylphenyl)carbamate.
38. 1-Methyl-2-propenyl N-(3,4-diethoxy-5-methylphenyl)carbamate.
39. 1-Methyl-2-propynyl N-(3,4-diethoxy-5-methylphenyl)carbamate.
40. 1-Methyl-2-methoxyethyl N-(3,4-diethoxy-5-methylphenyl)carbamate.
41. 4-Chloro-2-butynyl N-(3,4-diethoxy-5-methylphenyl)carbamate.
42. Isopropyl N-(3,4-diethoxy-5-ethylphenyl)carbamate.
43. Isopropyl N-(3,4-diethoxy-5-vinylphenyl)carbamate.
44. Isopropyl N-(3,4-diethoxy-5-methoxyphenyl)carbamate.
45. Isopropyl N-(3,4-diethoxy-5-methoxymethylphenyl)carbamate.
46. 1-Methyl-2-methoxyethyl N-(3,4-diethoxy-5-methoxymethylphenyl)carbamate.
47. Isopropyl N-(3-chloro-4-ethoxy-5-methoxymethylphenyl)carbamate.
48. Isopropyl N-(3,4-diethoxy-5-methoxycarbonylphenyl)carbamate.
49. Isopropyl N-(3-cyano-4,5-diethoxyphenyl)carbamate.
50. Isopropyl N-(3-methyl-4-ethoxy-5-methoxymethylphenyl)carbamate.
51. Isopropyl N-(3-methyl-4-ethoxy-5-n-propylphenyl)carbamate.
52. Isopropyl N-(3,4-diethoxy-5-bromophenyl)carbamate.
53. Isopropyl N-(3-methyl-4-propynyloxy-5-ethoxyphenyl)carbamate.
54. Isopropyl N-(3,4-diethoxy-5-acetylphenyl)carbamate.
55. Isopropyl N-[3,4-diethoxy-5-(1,2-dibromoethyl)-phenyl]carbamate.
56. Isopropyl N-(3-chloro-4-propynyloxy-5-methoxyphenyl)carbamate.
57. Isopropyl N-(3,4-diethoxy-5-dimethoxymethylphenyl)carbamate.
58. Isopropyl N-(3-chloro-4-ethoxy-5-n-propylphenyl)carbamate.
59. Isopropyl N-(3-bromo-4-ethoxy-5-methoxyphenyl)carbamate.
60. Isopropyl N-(3,5-diethyl-4-ethoxyphenyl)carbamate.
61. Isopropyl N-(3-chloro-4-ethoxy-5-methylphenyl)carbamate.
62. Isopropyl N-(3-methyl-4-ethoxy-5-allylphenyl)carbamate.
63. The fungicidal composition which comprises as an active ingredient a fungicidally effective amount of an N-phenylcarbamate of the formula:

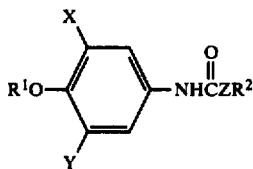

wherein X and Y, which may be the same or different, are each a halogen atom, a lower alkyl group, a lower alkenyl group, a lower cyanoalkenyl group, a lower alkynyl group, a lower alkoxy group, a cyano group, a lower alkyl group substituted with at least one member selected from the group consisting of halogen, hydroxyl and cyano, or a group of the formula:

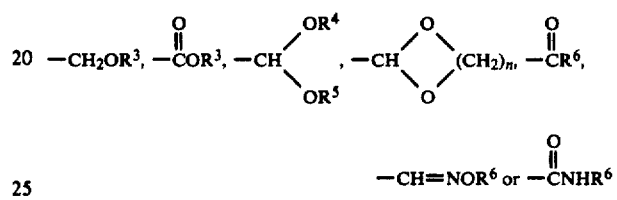

$$-CH=NOR^6 \text{ or } -\overset{O}{\underset{\|}{C}}NHR^6$$

in which $R^3$ is a lower alkyl group, a lower alkenyl group, a lower alkynyl group or a lower haloalkyl group, $R^4$ and $R^5$, which may be the same or different, are each a lower alkyl group, $R^6$ is a hydrogen atom or a lower alkyl group, n is 2, 3 or 4, Z is an oxygen atom or a sulfur atom, $R^1$ is a lower alkyl group, a lower alkenyl group, a lower alkynyl group or a lower alkyl group substituted with at least one member selected from the group consisting of halogen, lower alkoxy and lower cycloalkyl and $R^2$ is a $C_1$-$C_8$ alkyl group, a $C_3$-$C_8$ alkenyl group, a $C_3$-$C_8$ alkynyl group, a lower cycloalkyl group, a lower haloalkenyl group, a lower haloalkynyl group or a lower alkyl group substituted with at least one member selected from the group consisting of halogen, cyano, lower alkoxy, lower alkenyloxy, lower haloalkoxy group, phenoxy, lower aralkyloxy and lower cycloalkyl, and an inert carrier or diluent, and further comprises as an additional active ingredient(s) a benzimidazole thiophanate fungicide and/or a cyclic imide fungicide.

64. The fungicidal composition according to claim 63, wherein the benzimidazole thiophanate fungicide includes methyl 1-(butylcarbamoyl)benzimidazol-2-ylcarbamate, 2-(2-furyl)benzimidazole, 2-(4-thiazolyl)-benzimidazole, methyl benzimidazol-2-ylcarbamate, 1,2-bis(3-methoxycarbonyl-2-thioureido)benzene, 1,2-bis(3-ethoxycarbonyl-2-thioureido)benzene, 2-(O,S-dimethylphosphorylamino)-1-(3'-methoxycarbonyl-2'-thioureido)benzene or 2-(O,O-dimethylthiophosphorylamino)-1-(3'-methoxycarbonyl-2'-thioureido)-benzene and said cyclic imide fungicide includes 3-(3',5'-dichlorophenyl)-1,2-dimethylcyclopropane-1,2-dicarboximide, 3-(3',5'-dichlorophenyl)-1-isopropylcarbamoylimidazolidine-2,4-dione, 3-(3',5'-dichlorophenyl)-5-methyl-5-vinyloxazoline-2,4-dione or ethyl (RS)-3-(3',5'l -dichlorophenyl)-5-methyl-2,4-dioxooxazolidine-5-carboxylate.

65. A method for controlling plant pathogenic fungi which comprises applying a fungicidally effective amount of at least one of the N-phenylcarbamates of the formula:

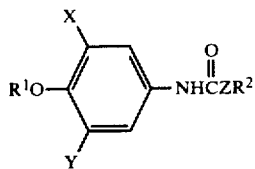

wherein X and Y, which may be the same or different, are each a halogen atom, a lower alkyl group, a lower alkenyl group, a lower cyanoalkenyl group, a lower alkynyl group, a lower alkoxy group, a cyano group, a lower alkyl group substituted with at least one member selected from the group consisting of halogen, hydroxyl and cyano, or a group of the formula:

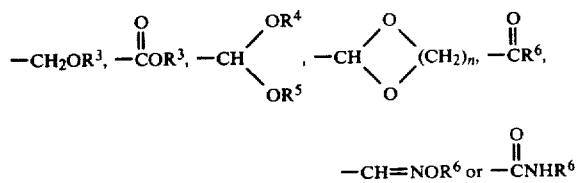

in which $R^3$ is a lower alkyl group, a lower alkenyl group, a lower alkynyl group or a lower haloalkyl group, $R^4$ and $R^5$, which may be the same or different, are each a lower alkyl group, $R^6$ is a hydrogen atom or a lower alkyl group, n is 2, 3, or 4, Z is an oxygen atom or a sulfur atom, $R^1$ is a lower alkyl group, a lower alkenyl group, a lower alkynyl group or a lower alkyl group substituted with at least one member selected from the group consisting of halogen, lower alkoxy and lower cycloalkyl and $R^2$ is a $C_1$-$C_8$ alkyl group, a $C_3$-$C_8$ alkenyl group, a $C_1$-$C_8$ alkynyl group, a lower cycloalkyl group, a lower haloalkenyl group, a lower haloalkynyl group or a lower alkyl group substituted with at least one member selected from the group consisting of halogen, cyano, lower alkoxy, lower alkenyloxy, lower haloalkoxy group, phenoxy, lower aralkyloxy and lower cycloalkyl, to plant pathogenic fungi.

66. The method according to claim 65, wherein the plant pathogenic fungi is the drug-resistant strain.

67. A method for controlling plant pathogenic fungi which comprises applying a fungicidally effective amount of a mixture of the N-phenylcarbamate of the formula:

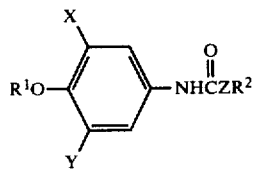

wherein X and Y, which may be the same or different, are each a halogen atom, a lower alkyl group, a lower alkenyl group, a lower cyanoalkenyl group, a lower alkynyl group, a lower alkoxy group, a cyano group, a lower alkyl group substituted with at least one member selected from the group consisting of halogen, hydroxyl and cyano, or a group of the formula:

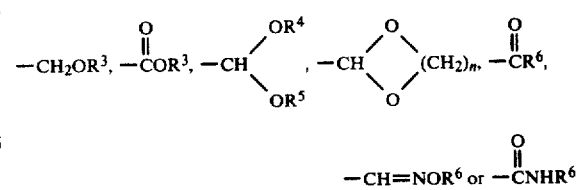

in which $R^3$ is a lower alkyl group, a lower alkenyl group, a lower alkynyl group or a lower haloalkyl group, $R^4$ and $R^5$, which may be the same or different, are each a lower alkyl group, $R^6$ is a hydrogen atom or a lower alkyl group, n is 2, 3 or 4, Z is an oxygen atom or a sulfur atom, $R^1$ is a lower alkyl group, a lower alkenyl group, a lower alkynyl group or a lower alkyl group substituted with at least one member selected from the group consisting of halogen, lower alkoxy and lower cycloalkyl and $R^2$ is a $C_1$-$C_8$ alkyl group, a $C_3$-$C_8$ alkenyl group, a $C_3$-$C_8$ alkynyl group, a lower cycloalkyl group, a lower haloalkenyl group, a lower haloalkynyl group or a lower alkyl group substituted with at least one member selected from the group consisting of halogen, cyano, lower alkoxy, lower alkenyloxy, lower haloalkoxy group, phenoxy, lower aralkyloxy and lower cycloalkyl, and a benzimidazole thiophanate fungicide and/or a cyclic imide fungicide.

* * * * *